미국 특허 US008162827B2

(12) United States Patent
Abdelgany et al.

(10) Patent No.: US 8,162,827 B2
(45) Date of Patent: Apr. 24, 2012

(54) ADJUSTABLE POLYAXIAL TISSUE RETRACTOR

(75) Inventors: Mahmoud F. Abdelgany, Rockaway, NJ (US); YoungHoon Oh, Montville, NJ (US); Kevin Sichler, West Orange, FL (US)

(73) Assignee: Custom Spine, Inc., Parsippany, NJ (US)

( * ) Notice: Subject to any disclaimer, the term of this patent is extended or adjusted under 35 U.S.C. 154(b) by 484 days.

(21) Appl. No.: 12/501,990

(22) Filed: Jul. 13, 2009

(65) Prior Publication Data

US 2011/0009706 A1 Jan. 13, 2011

(51) Int. Cl.
*A61B 1/32* (2006.01)
(52) U.S. Cl. ...................................................... 600/233
(58) Field of Classification Search .......... 600/201–246; 403/321, 322.4, 122–166
See application file for complete search history.

(56) References Cited

U.S. PATENT DOCUMENTS

| | | | |
|---|---|---|---|
| 3,749,088 A * | 7/1973 | Kohlmann | 600/215 |
| 4,566,663 A * | 1/1986 | Barchus | 248/324 |
| 5,052,374 A * | 10/1991 | Alvarez-Jacinto | 600/218 |
| 5,944,658 A | 8/1999 | Koros et al. | |
| 6,241,659 B1 | 6/2001 | Bookwalter et al. | |
| 6,458,079 B1 | 10/2002 | Cohn et al. | |
| 6,530,883 B2 | 3/2003 | Bookwalter et al. | |
| 7,156,805 B2 | 1/2007 | Thalgott et al. | |
| 7,182,729 B2 | 2/2007 | Abdelgany et al. | |
| 7,435,219 B2 | 10/2008 | Kim | |
| 7,491,168 B2 | 2/2009 | Raymond et al. | |
| 2008/0131198 A1 * | 6/2008 | Burrows | 403/322.4 |

* cited by examiner

*Primary Examiner* — Nicholas Woodall
(74) *Attorney, Agent, or Firm* — Rahman LLC

(57) ABSTRACT

An adjustable polyaxial tissue retractor includes a retraction bar including a plurality of etched teeth, a retraction blade coupled to the retraction bar, a connector including a quick release component cavity and an outwardly protruding and expandable round bulbous body, a quick release component engaged with at least one tooth of the retraction bar via a retraction bar cavity, where the quick release component is configured to loosely mate with the quick release component cavity, a saddle pin engaged within the connector via a first channel bored through the connector and contacting the bulbous body causing the bulbous body to outwardly expand, and a base including a plurality of embedded sockets and directly connected to the bulbous body, where the base receives the connector.

19 Claims, 22 Drawing Sheets

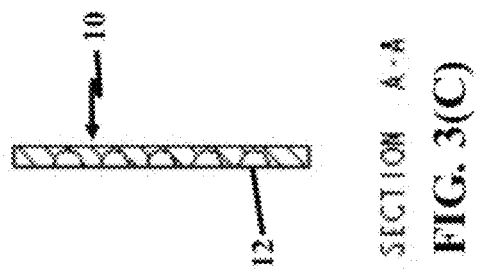
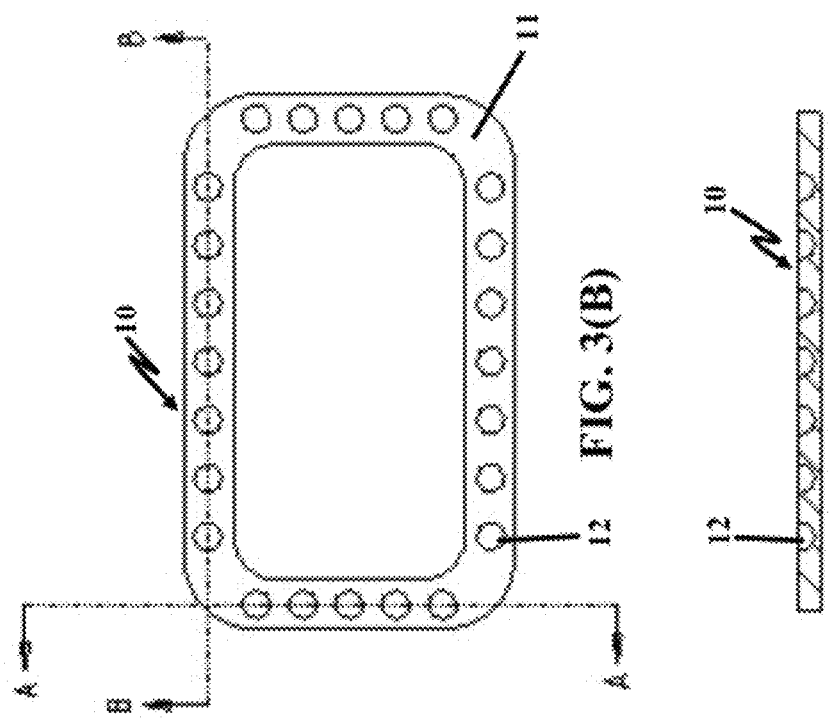
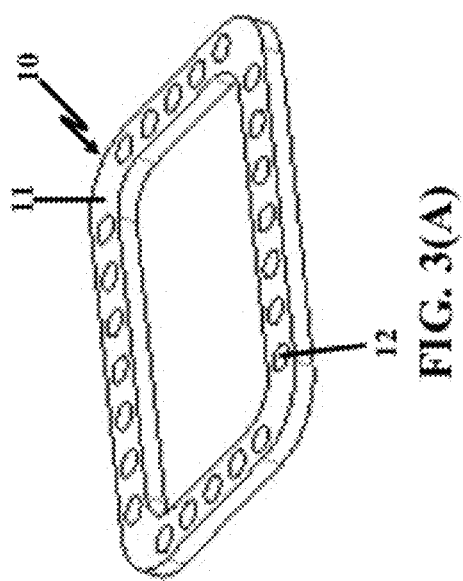

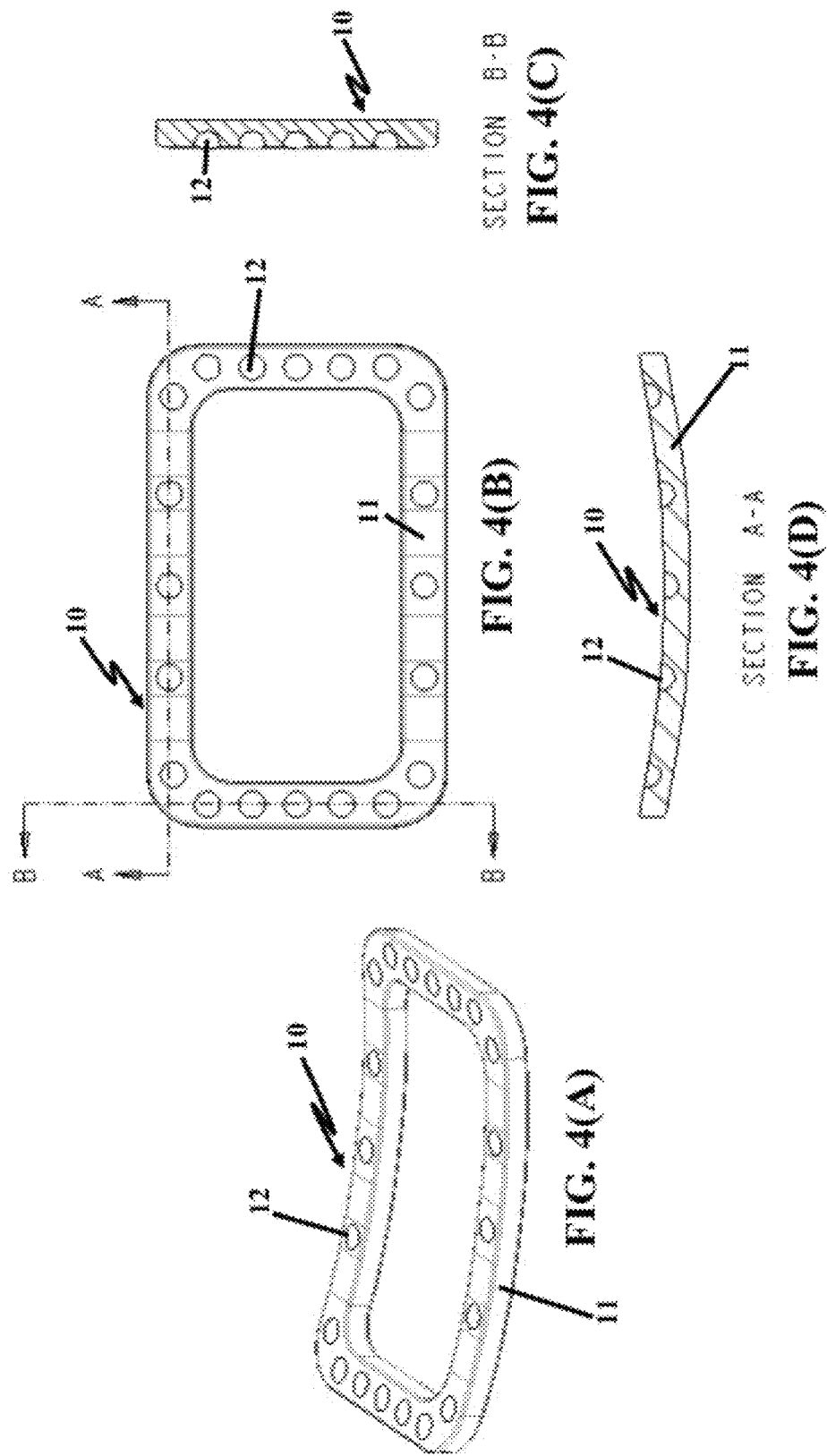

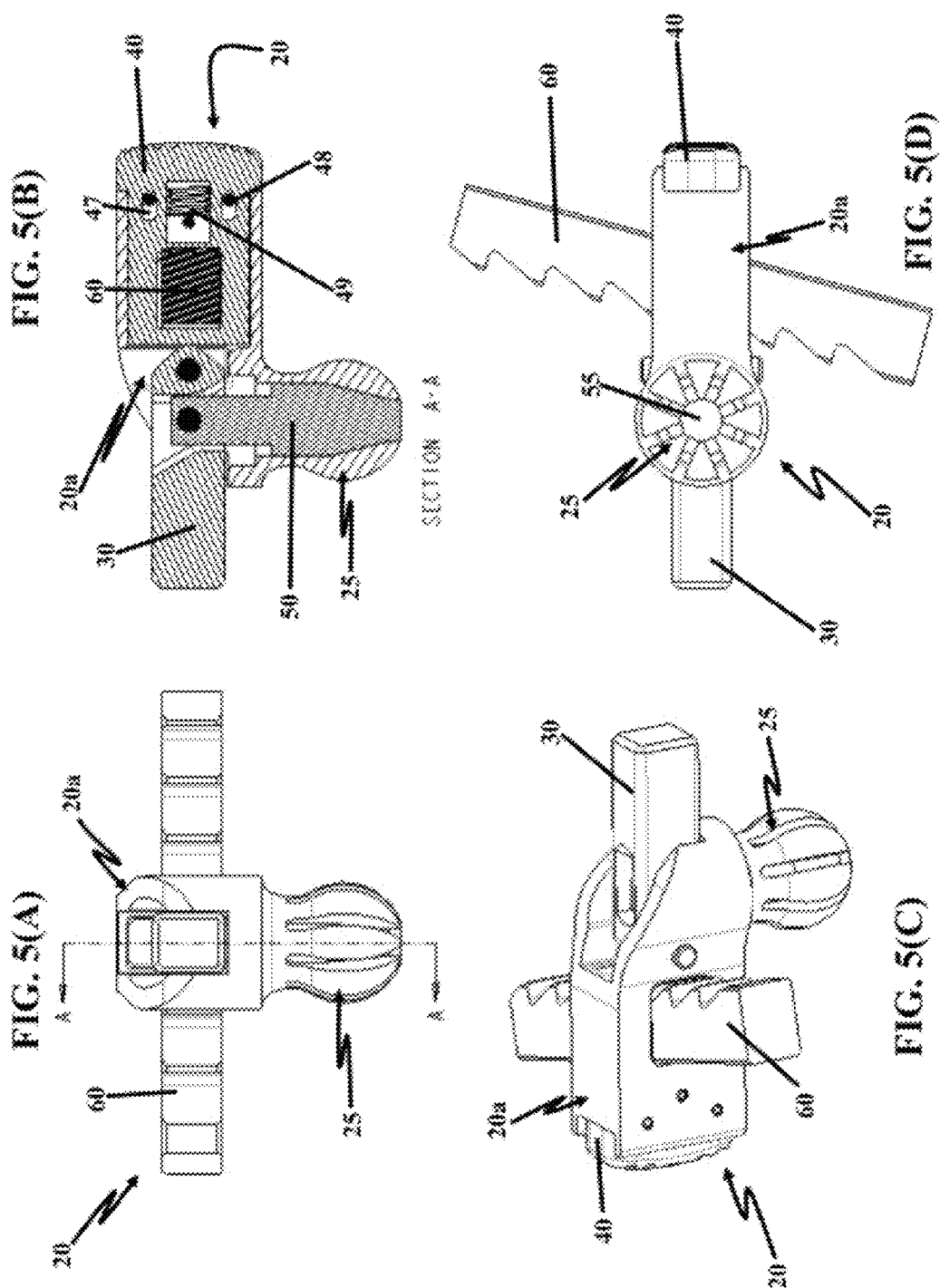

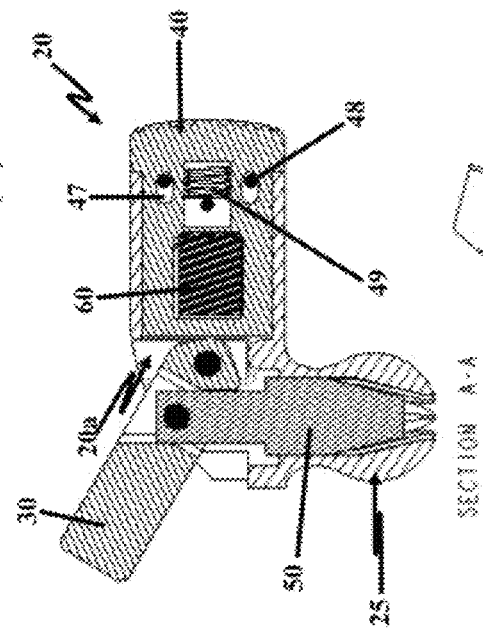
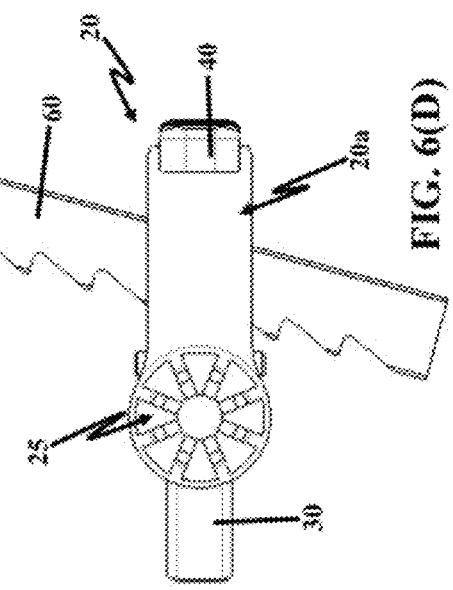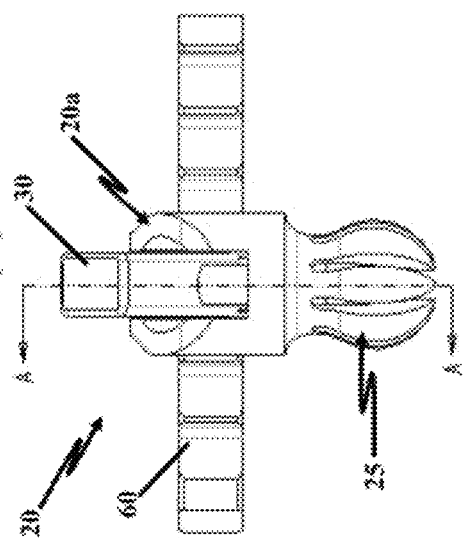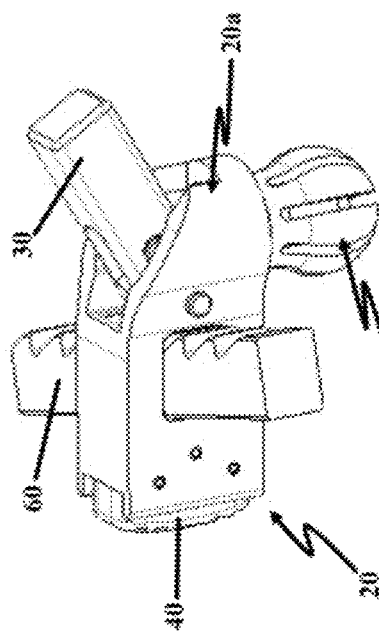

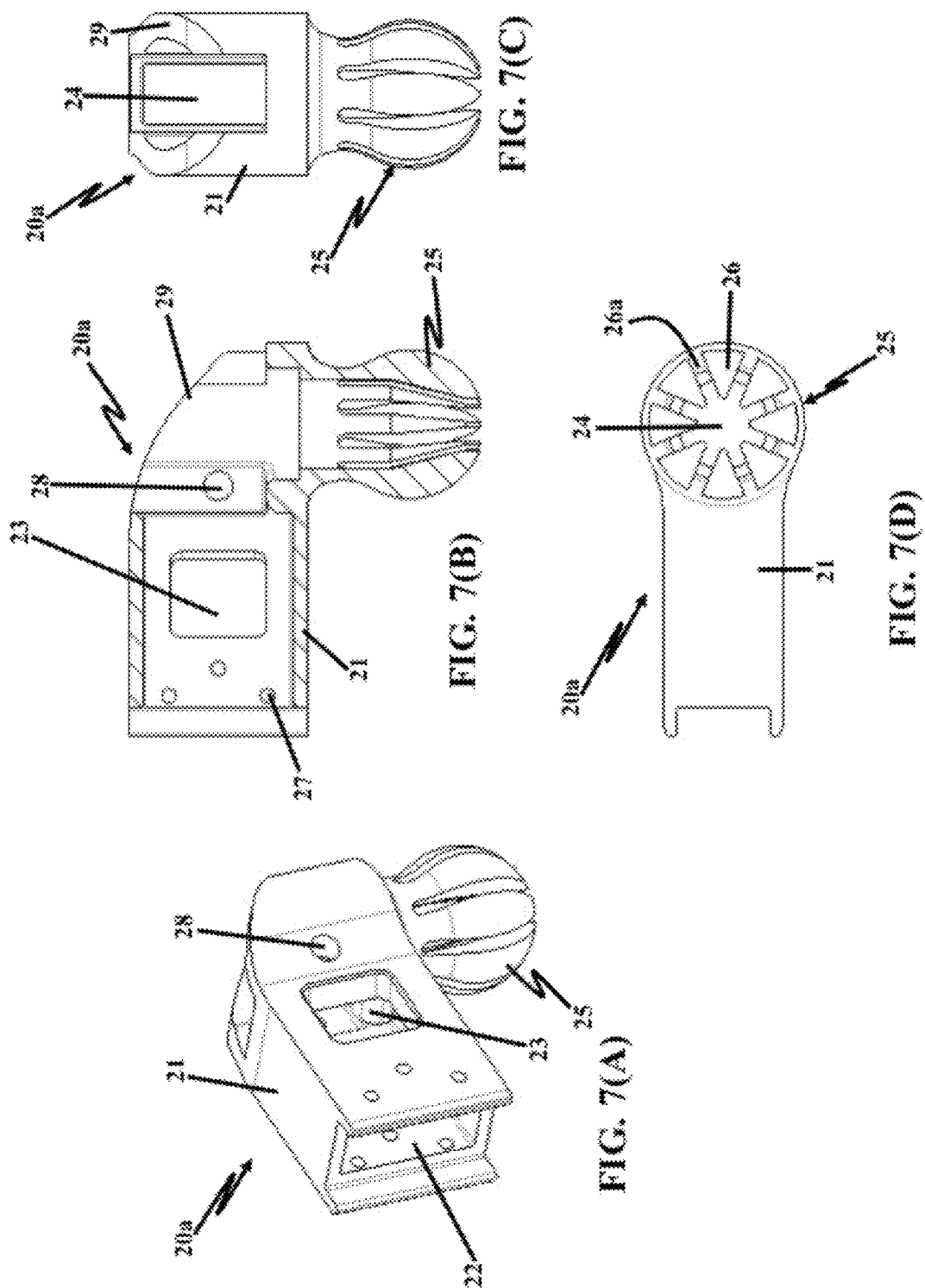

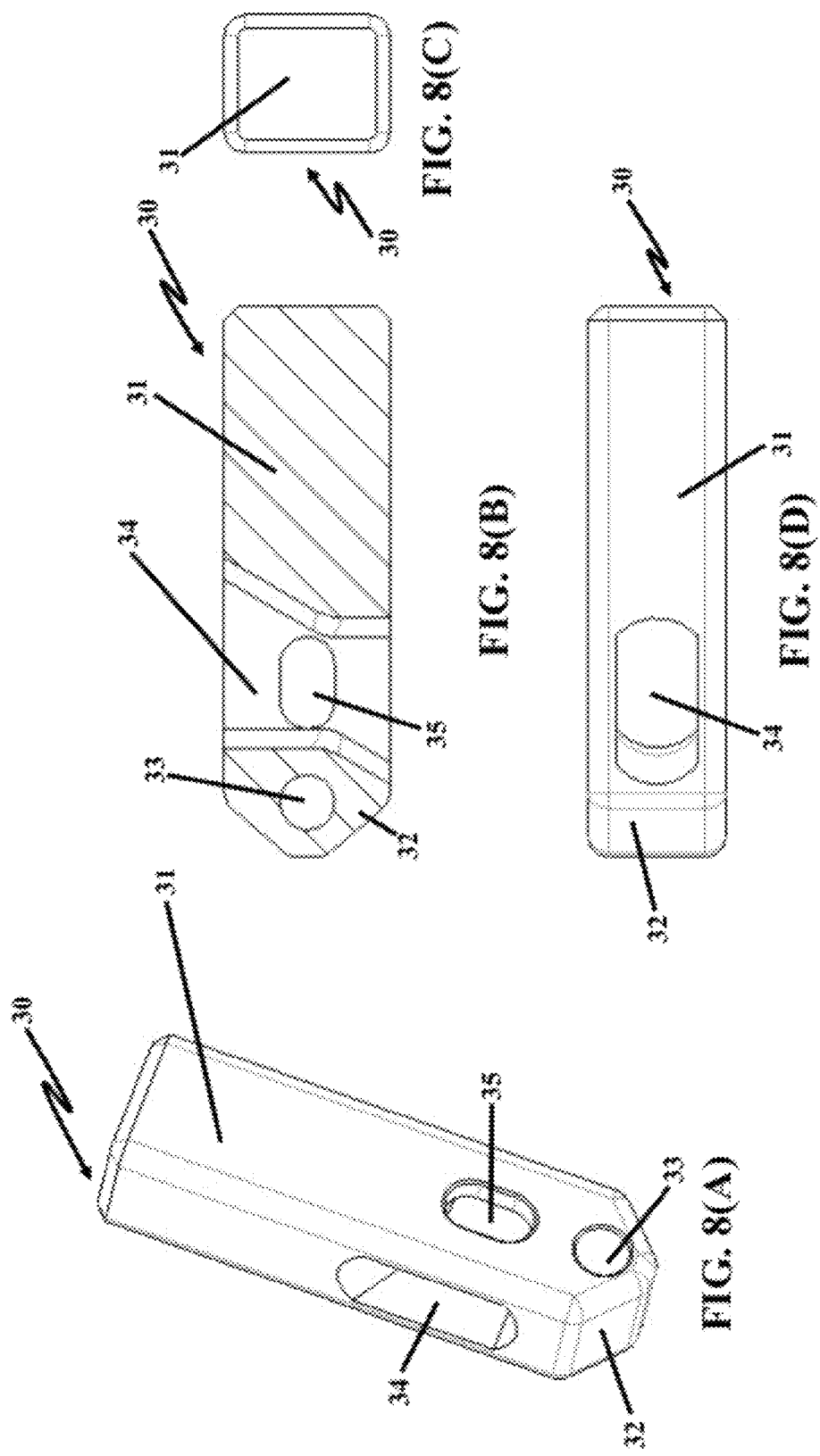

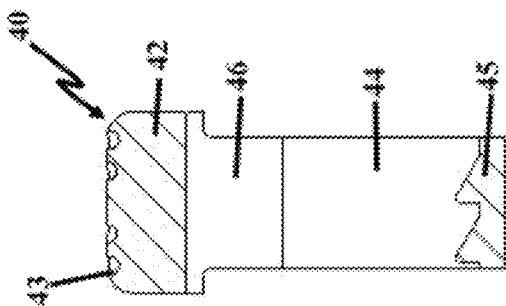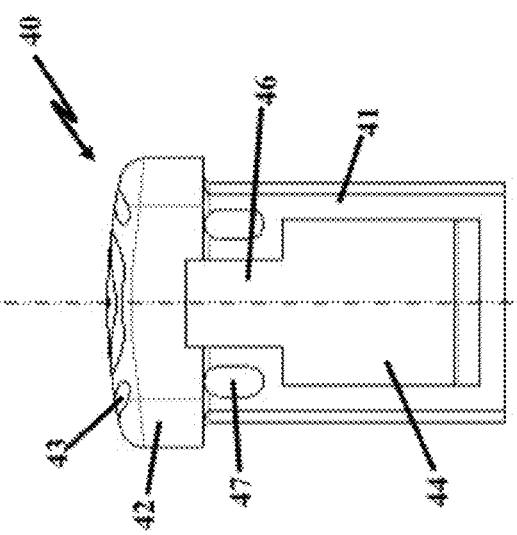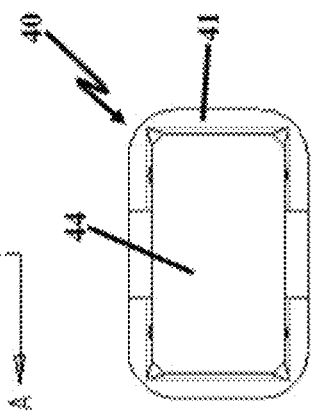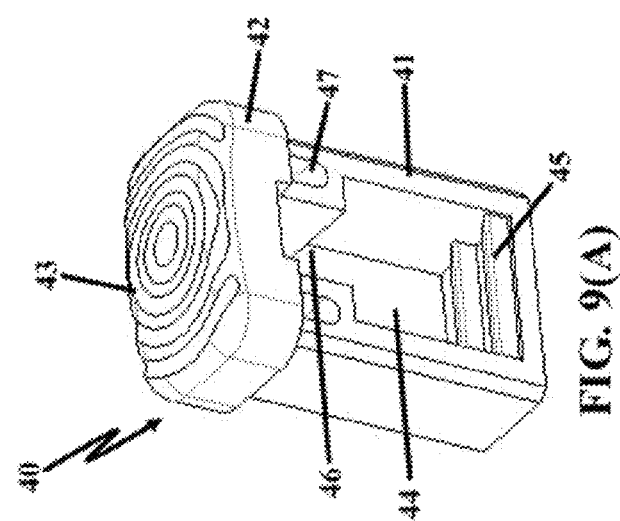

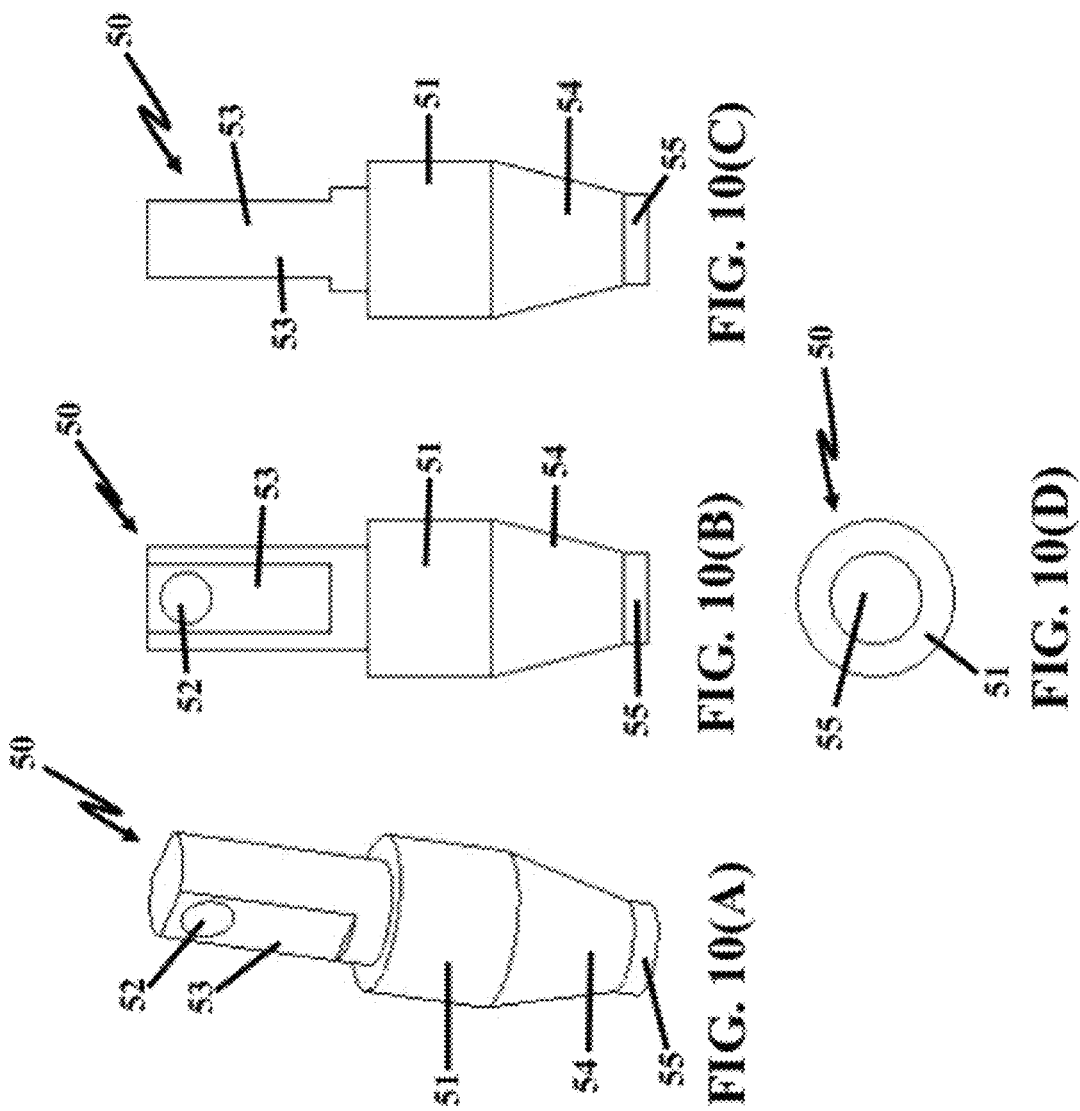

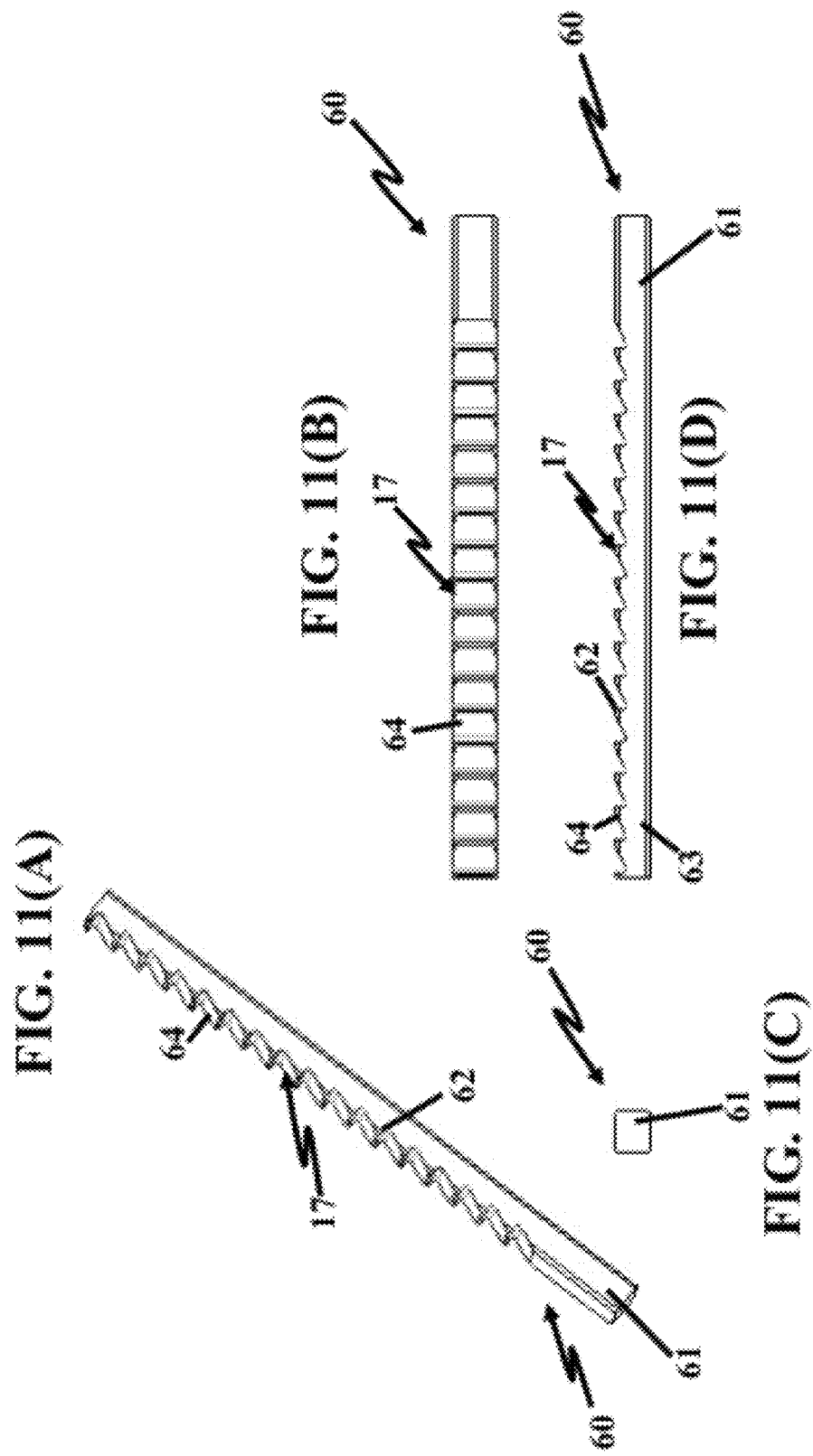

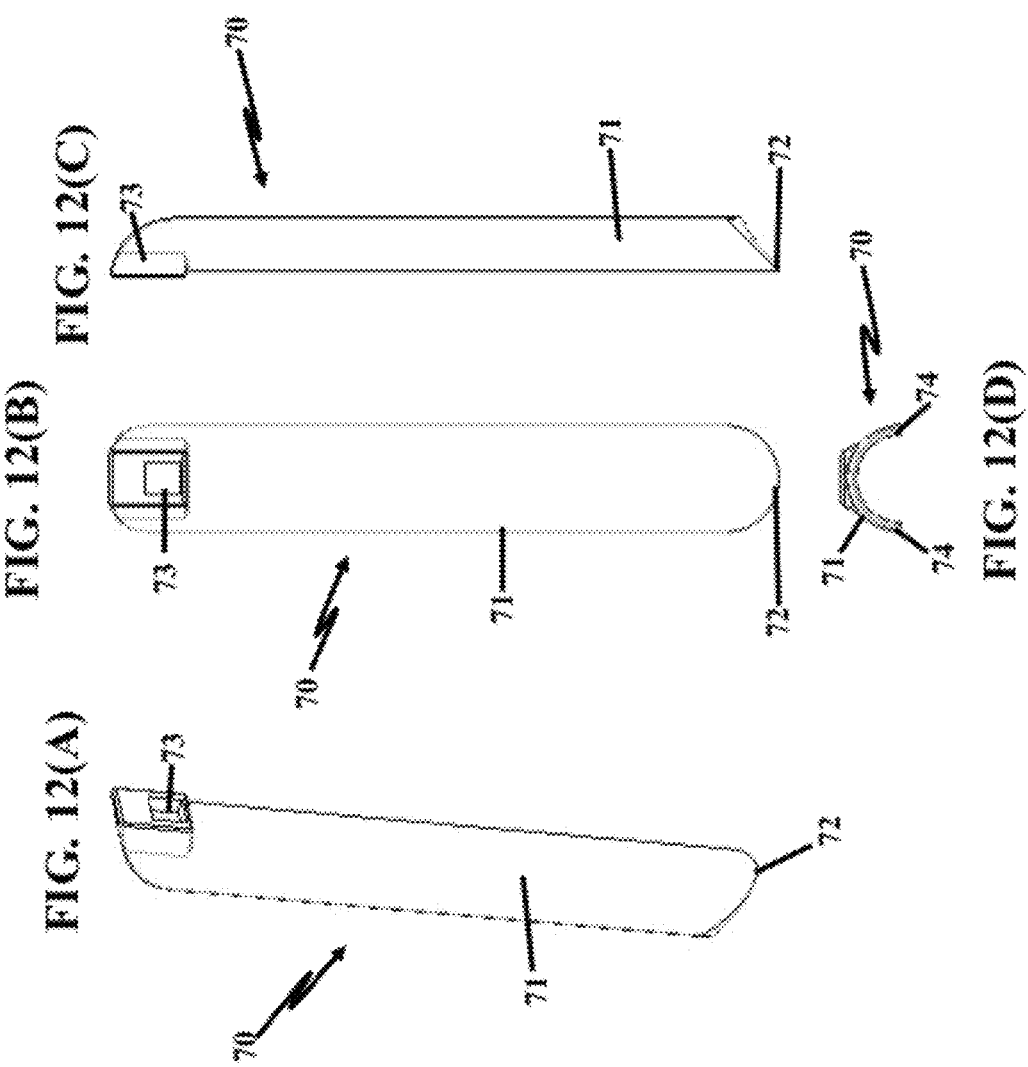

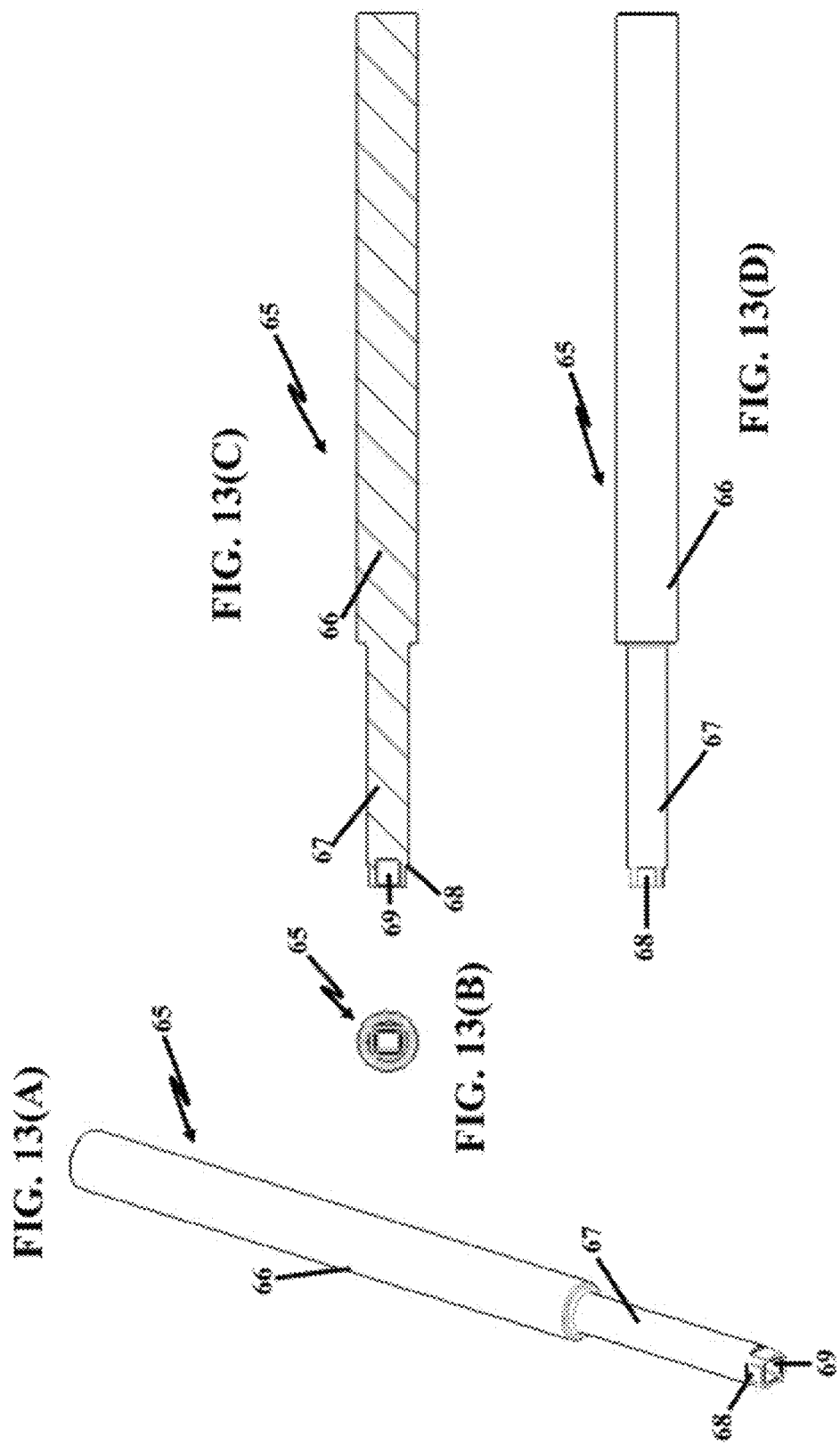

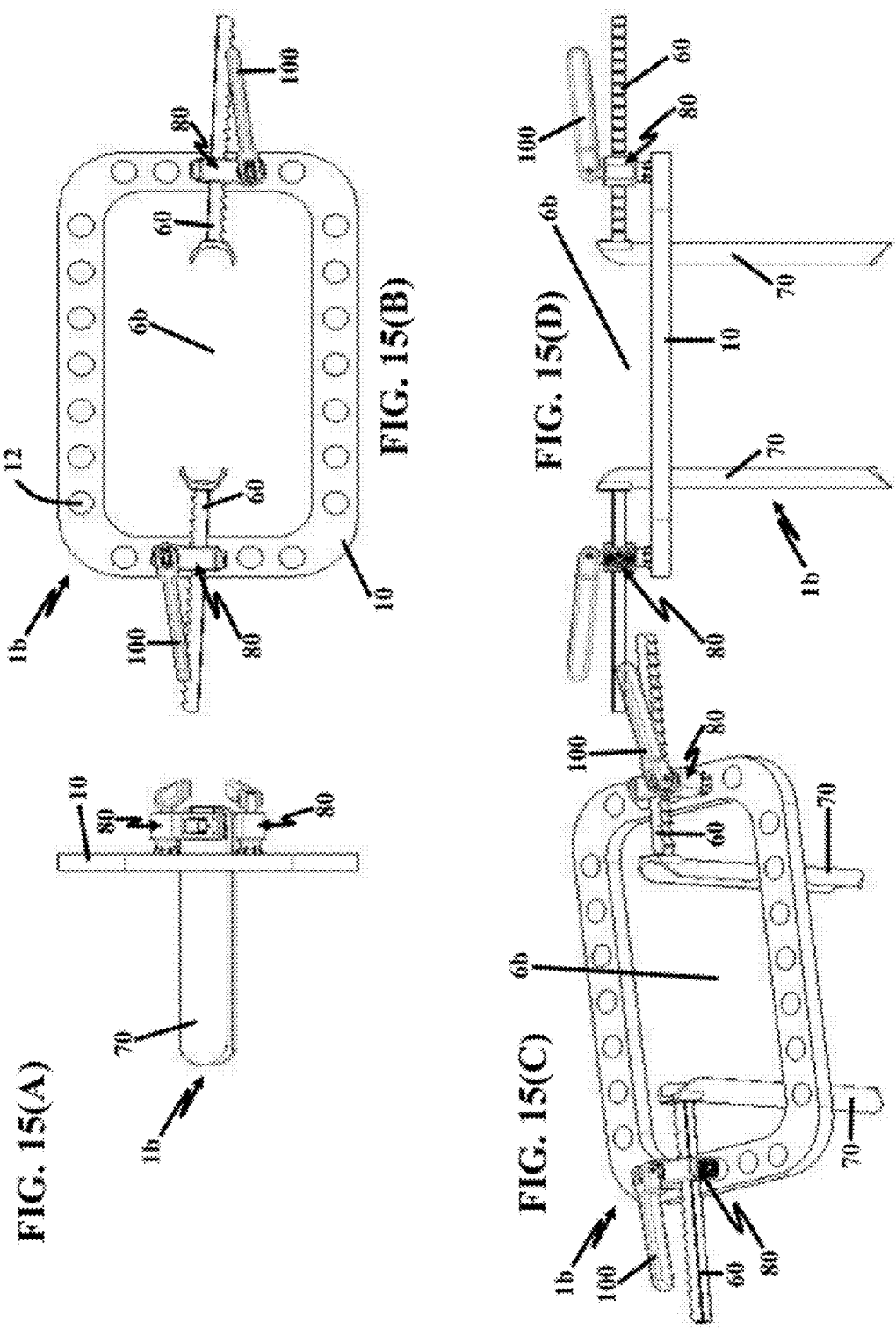

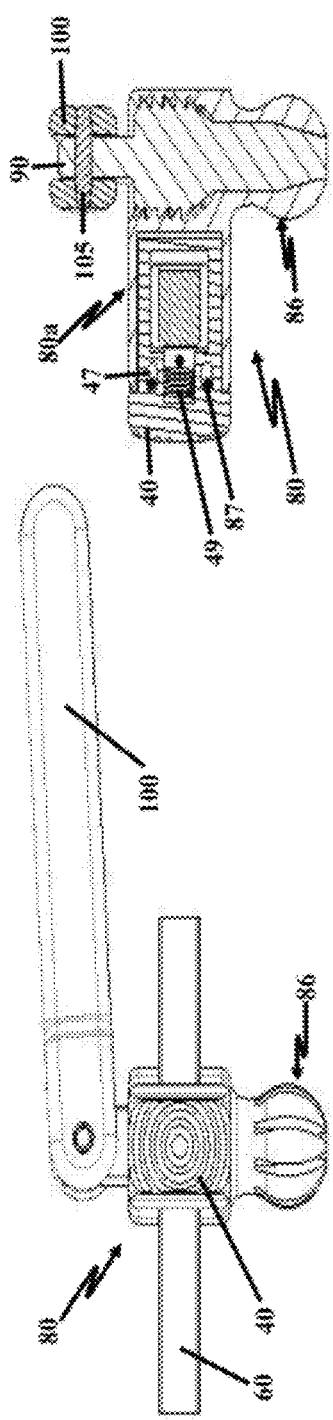
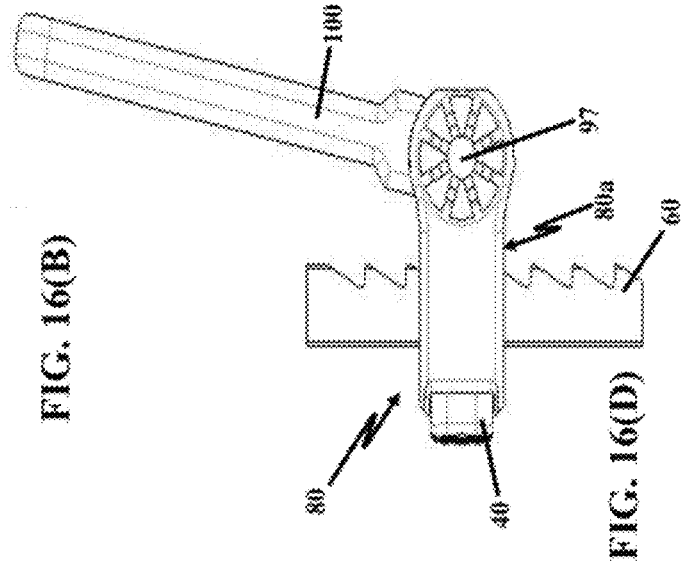
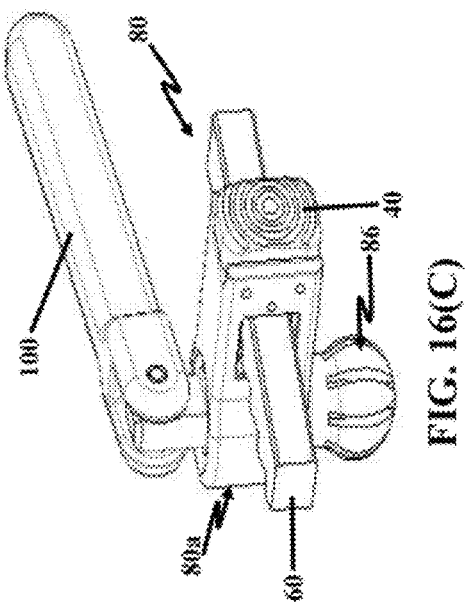
FIG. 16(A)
FIG. 16(B)
FIG. 16(C)
FIG. 16(D)

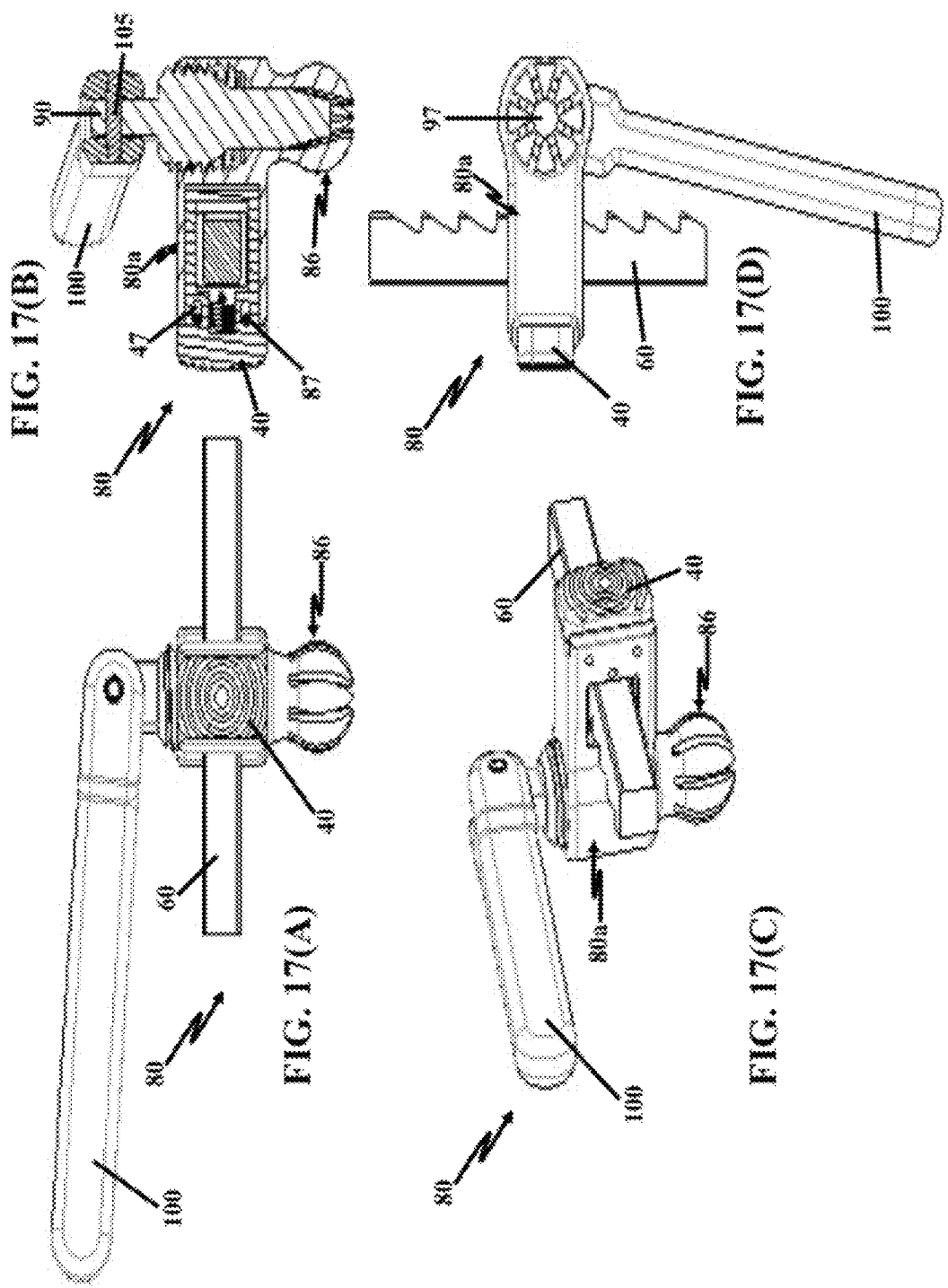

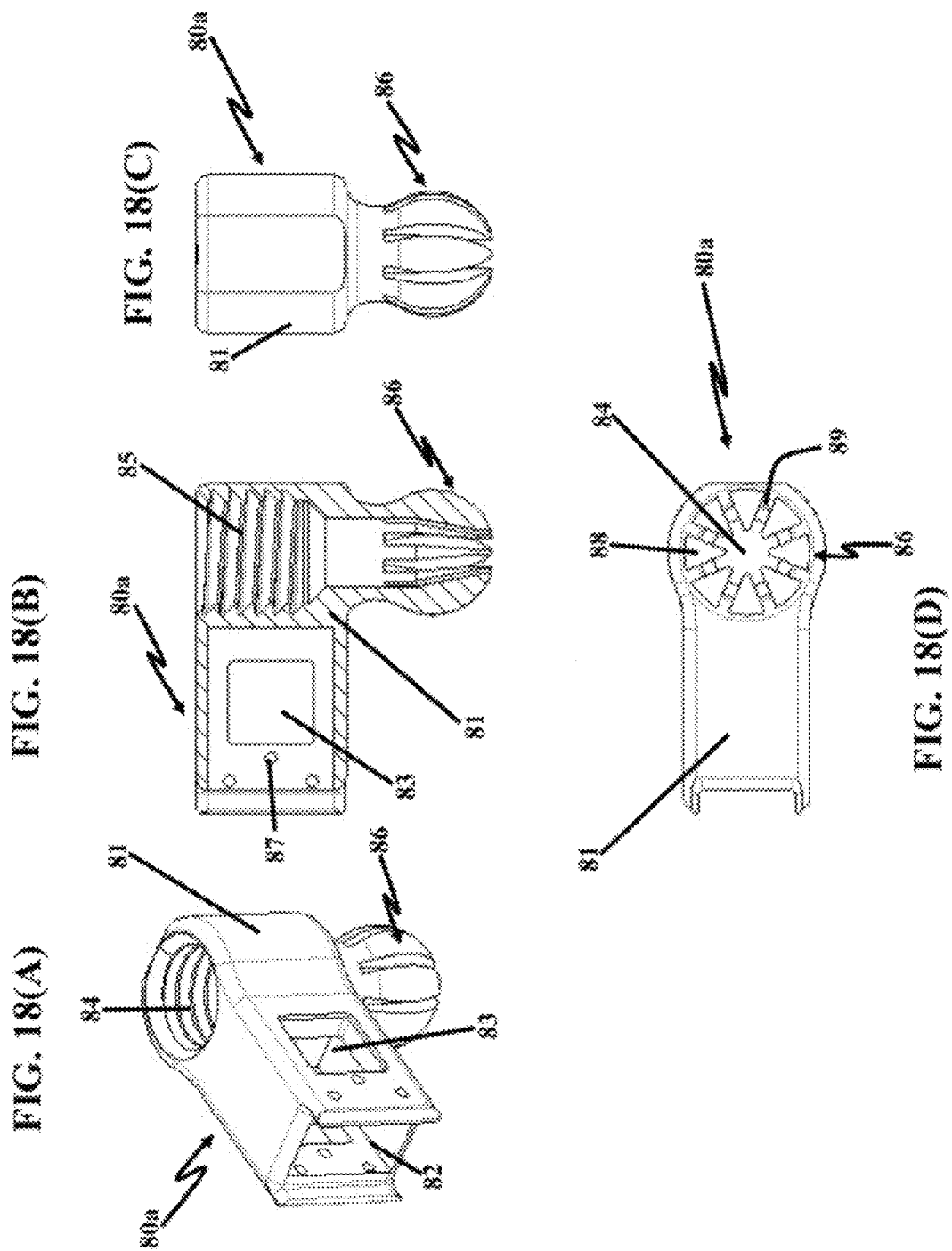

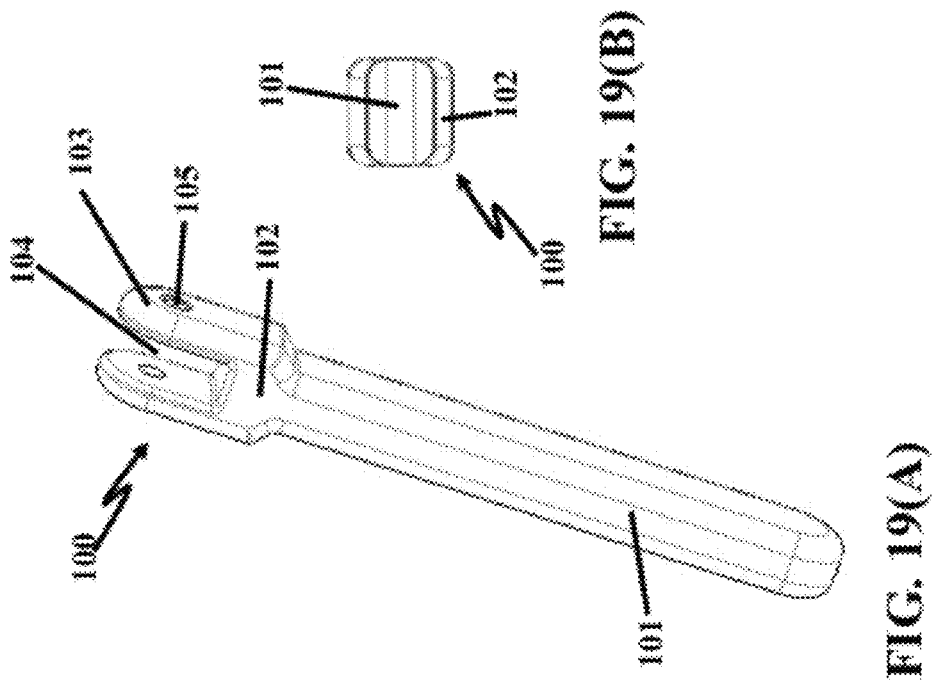

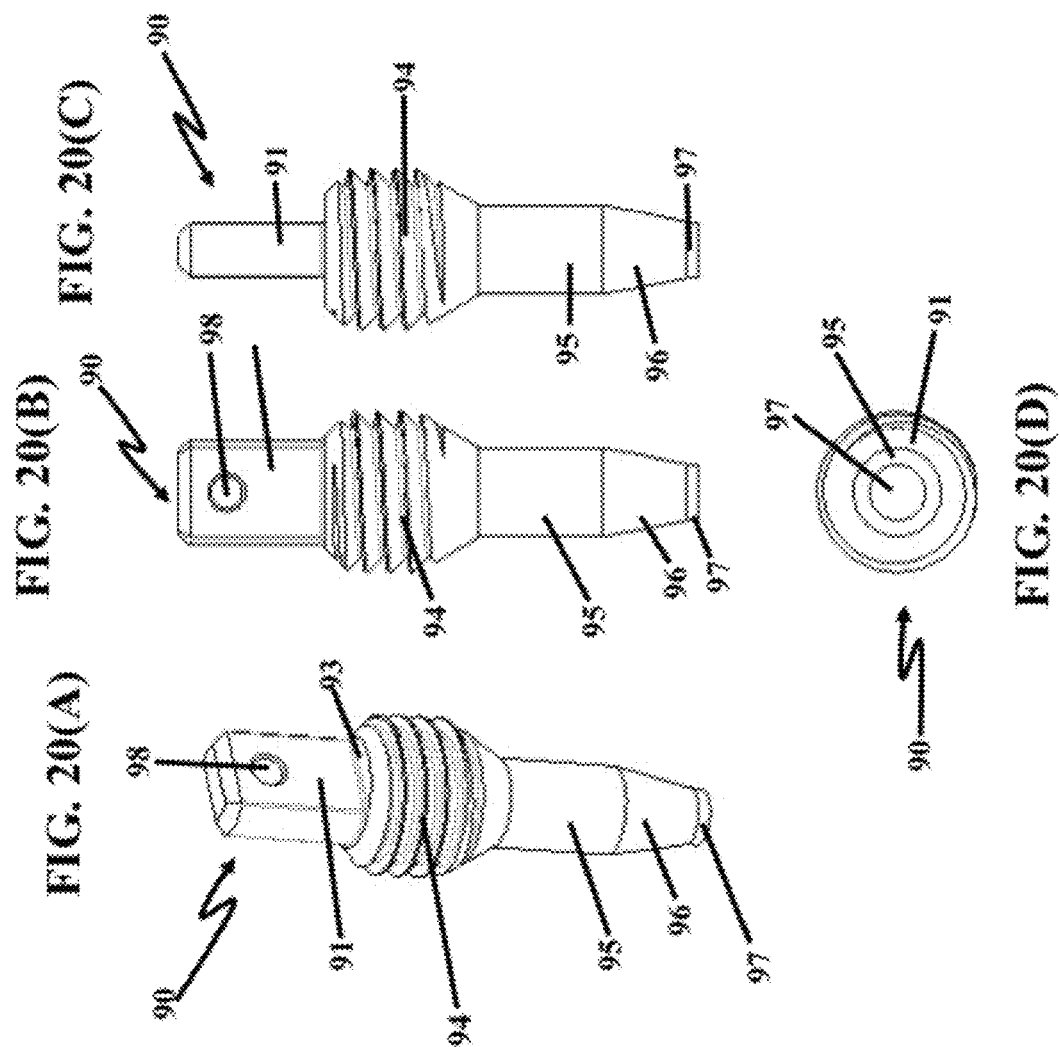

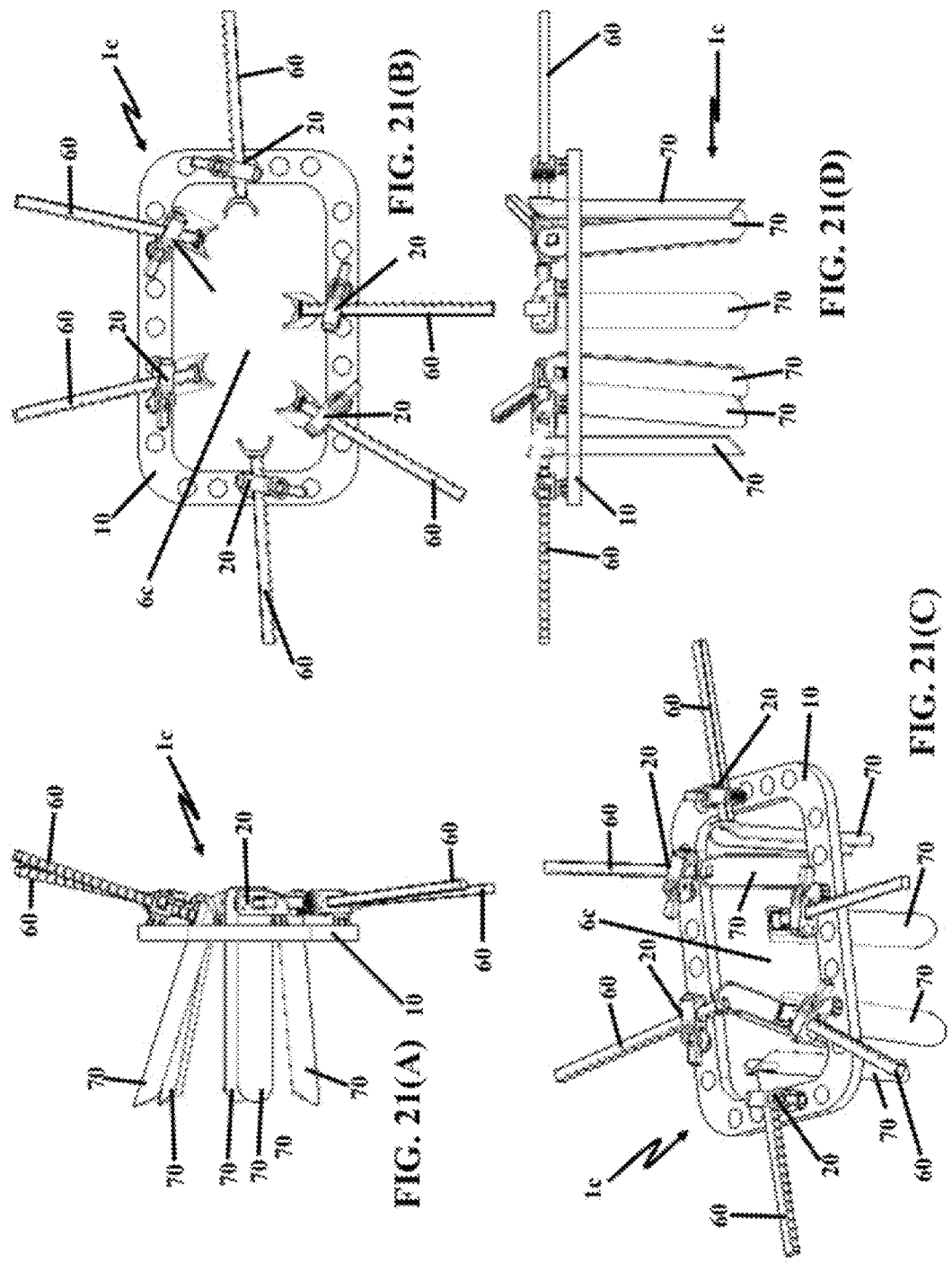

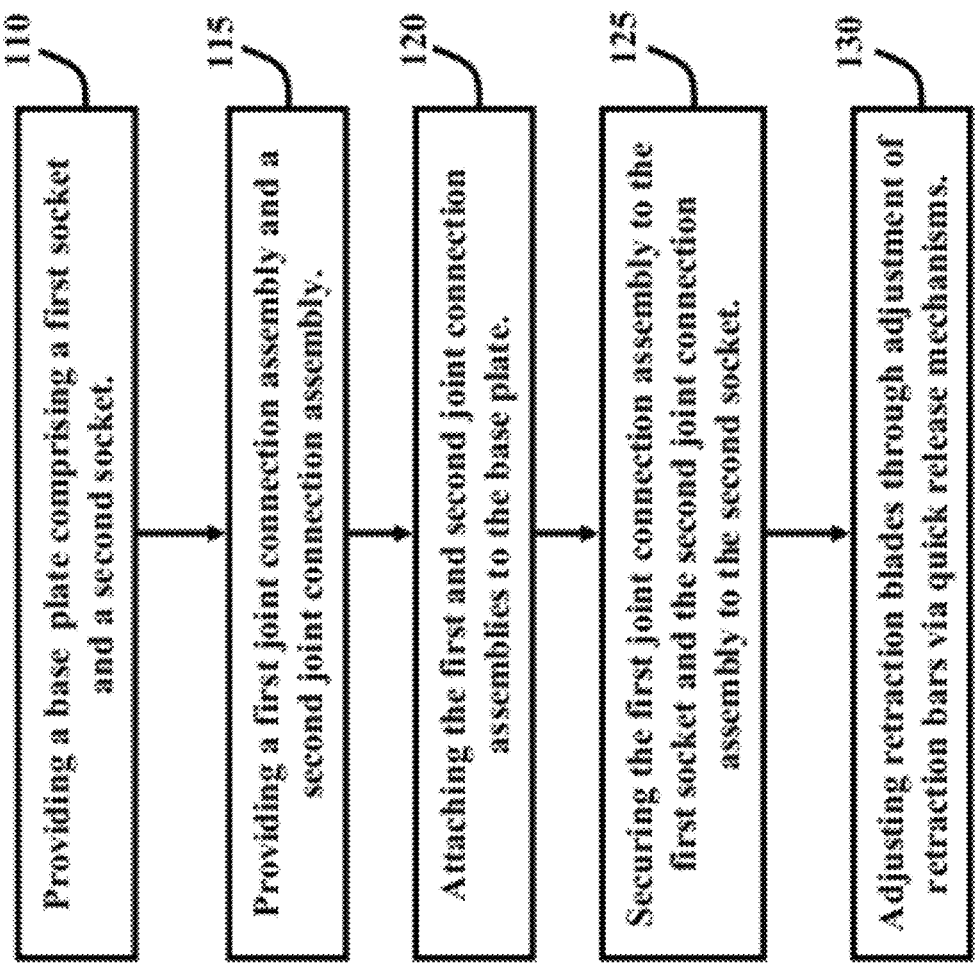

ADJUSTABLE POLYAXIAL TISSUE RETRACTOR

BACKGROUND

1. Technical Field

The embodiments herein generally relate to medical devices, and, more particularly, to tissue retraction devices and retraction devices for the spine.

2. Description of the Related Art

Traditional surgical procedures for pathologies located within the body can cause significant trauma to the intervening tissues. These procedures often require a long incision, extensive muscle stripping, prolonged retraction of tissues, denervation, and devascularization of tissue. These procedures can require operating room time of several hours and several weeks of post-operative recovery time due to the destruction of tissue during the surgical procedure. In some cases, these invasive procedures lead to permanent scarring and pain that can be more severe than the pain leading to the surgical intervention.

The development of percutaneous procedures has yielded a major improvement in reducing recovery time and post-operative pain because minimal dissection of tissue, such as muscle tissue, is required. For example, minimally invasive surgical techniques are desirable for spinal and neurosurgical applications because of the need for access to locations within the body and the danger of damage to vital intervening tissues. While developments in minimally invasive surgery are steps in the right direction, there remains a need for further development in minimally invasive surgical instruments and methods. For example, conventional systems which employ minimally invasive surgical instruments are restricted to fewer than three degrees of freedom. Stated another way, conventional tissue retraction devices typically only allow precise adjustment of one articulated components before and/or during a surgical procedure. What is needed is a system that provides additional freedom to a surgeon before and/or during a surgical procedure by offering greater articulation and more degrees of freedom, which can be exploited by the surgeon under a controlled surgical environment.

SUMMARY

In view of the foregoing, an embodiment herein provides a system for retracting tissue, the system comprising a retraction bar including a plurality of teeth etched therein; a retraction blade coupled to the retraction bar; a connector including a quick release component cavity and an outwardly protruding and expandable round bulbous body; a quick release component engaged with at least one tooth of the retraction bar via a retraction bar cavity, where the quick release component is configured to loosely mate with the quick release component cavity; a saddle pin engaged within the connector via a first channel bored through the connector and contacting the bulbous body causing the bulbous body to outwardly expand; and a base including a plurality of sockets embedded therein and directly connected to the bulbous body, wherein the base receives the connector.

Embodiments described herein also provide a longitudinal cross-section of the base is concaved. Additionally, the base may comprise a socket that cups the expandable bulbous body of the connector. Moreover, the saddle pin may comprise a push-down saddle pin including a grooved upper portion and a smooth lower portion, and wherein the lower portion included a tapered section.

Furthermore, embodiments described herein may further comprise a push-down handle; a pivoting channel bored through the push-down handle; an axis channel bored through the connector; a pivoting pin configured to mate with the pivoting channel and the axis channel and thereby allowing the push-down handle to pivot with respect to the connector; a saddle-handle channel bored through the push-down handle, wherein the grooved upper portion of the push-down saddle pin is configured to mate with the saddle-handle channel; a locking saddle pin channel bored through the grooved upper portion of the push-down saddle pin; and a locking saddle pin configured to mate with the saddle-handle channel and the locking saddle pin channel. Such an embodiment may additionally provide a push-down assistance rod including an assistance socket, where the assistance socket is configured to mate with the grooved upper portion of the push-down saddle pin.

Moreover, in embodiments described herein, the saddle pin may comprise a threaded saddle pin including a lower portion and a threaded upper portion that is configured to mate with threads embedded in the first channel. Embodiments described herein may also further comprise a locking channel bored through the threaded upper portion; a threaded saddle handle; a saddle-handle pin channel bored through the threaded saddle handle; and a saddle-handle pin configured to mate with the locking channel and the saddle handle pin channel.

Additionally, embodiments described herein provide that the quick release component includes an upper portion and a lower portion, wherein the retraction bar cavity is cut into the lower portion. Such an embodiment may further comprise a spring cavity cut into the lower portion of the quick release component; and a spring embedded into the spring cavity. In addition, such an embodiment may further comprise a plurality of rivets, fixedly coupled to the quick-release component cavity of the connector; and a plurality of rivet channels, equal to the number of the rivets and bored through the lower portion of the quick release component, wherein each of the rivet channels is configured to mate with one of the rivets and the rivet channels allow lateral movement of the rivets. Moreover, such an embodiment may also further comprise concentric grooves etched onto an outer surface of the upper portion of the quick release component.

In addition, an embodiment herein provides a system for retracting tissue, the system comprising a retraction bar including a plurality of teeth etched therein; a retraction blade including a retraction bar socket bored through the retraction blade and configured to securely mate with the retraction bar; a connector including a quick release component cavity and an outwardly protruding and expandable round bulbous body; a quick release component engaged with at least one tooth of the retraction bar via a retraction bar cavity, where the quick release component is configured to loosely mate with the quick release component cavity; a base including a plurality of sockets embedded therein and directly connected to the bulbous body, wherein the base receives the connector; a saddle pin engaged within the connector via a first channel bored through the connector and contacting the bulbous body causing the bulbous body to outwardly expand, the saddle pin including an upper portion and a lower portion; a handle coupled to the saddle pin; and a base including a plurality of sockets embedded therein and directly connected to the bulbous body, wherein the base receives the connector.

In such an embodiment, the bulbous body may comprise a plurality of slots separating a plurality of bendable flanges of the bulbous body. Furthermore, such an embodiment may further comprise a plurality of connectors, wherein each connector includes an outwardly protruding and expandable round bulbous body coupled to a socket on the base. Moreover, in such an embodiment, the connector may comprises a substantially planar lower surface, wherein the bulbous body extends from the lower surface of the connector, and wherein a socket of the plurality of sockets embedded in the base cups the expandable bulbous body.

Furthermore, such an embodiment, as described above, may further comprise a pivoting channel bored through the handle; a push-down handle axis channel bored through the connector; a pivoting pin configured to mate with the pivoting channel and the axis channel and thereby allowing the handle to pivot with respect to the connector; a saddle-handle channel bored through the handle, wherein the upper portion of the saddle pin is configured to mate with the saddle-handle channel; a locking saddle pin channel bored through the upper portion of the saddle pin; and a locking saddle pin configured to mate with the saddle-handle channel and the locking saddle pin channel.

In addition, in such an embodiment, the first channel may be etched with first channel threads, and wherein the upper portion of the saddle pin is embedded with saddle pin threads configured to mate with the first channel threads. Moreover, such an embodiment may further comprise a locking channel bored through the upper portion of the saddle pin; a saddle-handle pin channel bored through the handle; and a saddle-handle pin configured to mate with the locking channel and the saddle handle pin channel.

In addition, embodiment herein also provides a method of retracting tissue, the method comprising providing a base plate comprising a first socket and a second socket; providing a first joint connection assembly and a second joint connection assembly, wherein each of the first and second joint connection assemblies comprise a retraction bar including a plurality of teeth etched therein; a retraction blade coupled to the retraction bar; a connector including a quick release component cavity and an outwardly protruding and expandable bulbous body, where the bulbous body is directly coupled to any of the first socket and the second socket; a quick release component operatively connected to the quick release component cavity and engaged with at least one tooth of the retraction bar via a retraction bar cavity, where the quick release component is configured to loosely mate with the quick release component cavity; and a saddle pin engaged within the connector via a first channel bored through the connector and contacting the bulbous body causing the bulbous body to outwardly expand; attaching the first and second joint connection assemblies to the base plate; securing the first joint connection assembly to the first socket and the second joint connection assembly to the second socket by inserting the saddle pin through a channel bored through the first joint connection assembly causing the bulbous body of the first joint connection assembly to outwardly expand into the first socket and causing the bulbous body of the second joint connection assembly to outwardly expand into the second socket; and adjusting the retraction blades through adjustment of the retraction bars via the quick release mechanisms, wherein engagement of the quick release mechanisms prevent the retraction bars from adjustment in a first longitudinal direction and allows adjustment of the retraction bars in a second longitudinal direction opposite of the first longitudinal direction, and wherein disengagement of the quick release mechanism allows adjustment of the retraction bars in the first and the second longitudinal directions.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIGS. 3(A) through 3(D) are schematic diagrams of a base plate, according to an embodiment described herein;

FIGS. 4(A) through 4(D) are additional schematic diagrams of a base plate, according to an embodiment described herein;

FIGS. 5(A) through 5(D) illustrate a push-down connection assembly with a push-down securing mechanism, in a closed configuration, according to an embodiment described herein;

FIGS. 6(A) through 6(D) illustrate a push-down connection assembly with a push-down securing mechanism, in an open configuration, according to an embodiment described herein;

FIGS. 7(A) through 7(D) are schematic diagrams of a connector with a push-down securing mechanism, according to an embodiment described herein;

FIGS. 8(A) through 8(D) are schematic diagrams of a push-down handle, according to an embodiment described herein;

FIGS. 9(A) through 9(D) are schematic diagrams of a quick release mechanism, according to an embodiment described herein;

FIGS. 10(A) through 10(D) are schematic diagrams of a push-down saddle pin, according to an embodiment described herein;

FIGS. 11(A) through 11(D) are schematic diagrams of a retraction bar, according to an embodiment described herein;

FIGS. 12(A) through 12(D) are schematic diagrams of a retraction blade, according to an embodiment described herein;

FIGS. 13(A) through 13(D) are schematic diagrams of a push-down assistance rod, according to an embodiment described herein;

FIG. 15(A) through 15(D) illustrate an adjustable polyaxial tissue retraction device, with two blades and a threaded securing mechanism, in an open configuration, according to an embodiment described herein;

FIGS. 16(A) through 16(D) illustrate a threaded connection assembly, with a threaded securing mechanism, in a closed configuration, according to an embodiment described herein;

FIGS. 17(A) through 17(D) illustrate a threaded connection assembly, with a threaded securing mechanism, in an open configuration, according to an embodiment described herein;

FIGS. 18(A) through 18(D) are schematic diagrams of a connector, with a threaded securing mechanism, according to an embodiment described herein;

FIGS. 19(A) through 19(D) are schematic diagrams of a threaded saddle pin, according to an embodiment described herein;

FIGS. 20(A) through 20(D) are schematic diagrams of a threaded saddle handle, according to an embodiment described herein;

FIGS. 21(A) through 21(D) are schematic diagrams illustrating an adjustable polyaxial tissue retraction device, with six blades and a push-down securing mechanism, in an open configuration, according to an embodiment described herein; and FIG. 22 is a flow diagram illustrating a method according to an embodiment described herein.

DETAILED DESCRIPTION OF PREFERRED EMBODIMENTS

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Figure 1A:
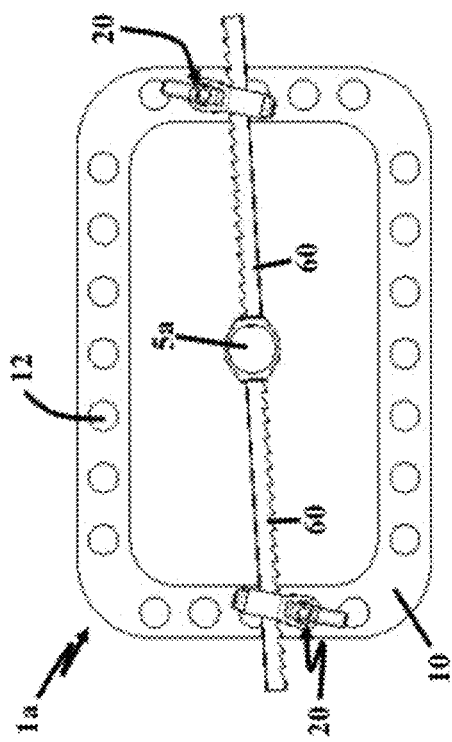
FIGS. 1(A) through 1(D) illustrate an adjustable polyaxial tissue retraction device, with two blades and a push-down securing mechanism, in a closed configuration, according to an embodiment described herein.
Figure 1B:
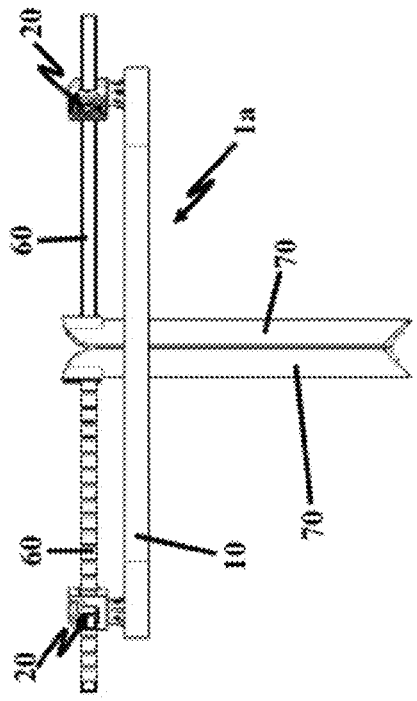
Figure 1C:
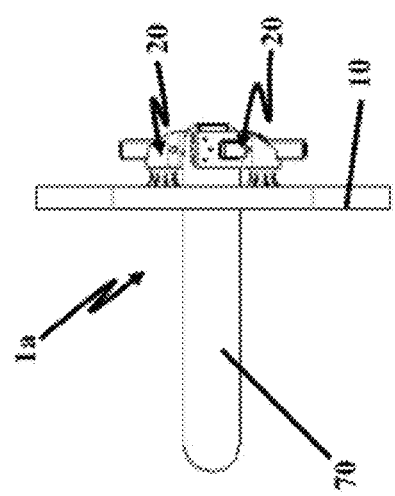
Figure 1D:
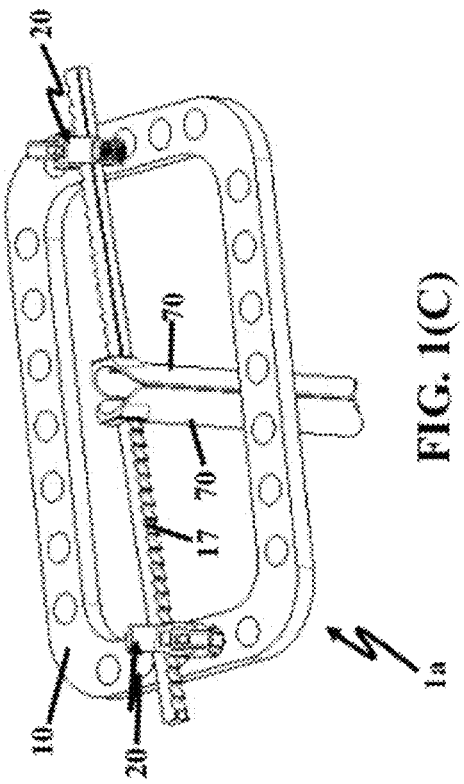
Figure 2A:
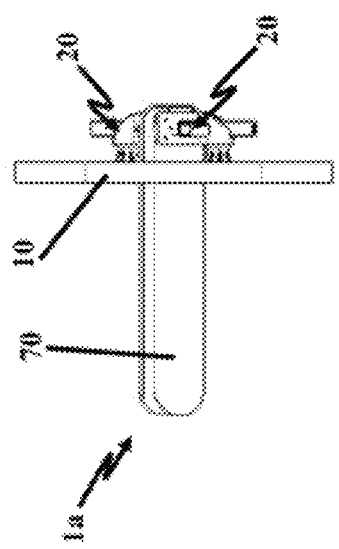
FIG. 2(A) through 2(D) illustrate an adjustable polyaxial tissue retraction device, with two blades and a push-down securing mechanism, in an open configuration, according to an embodiment described herein.
Figure 2B:
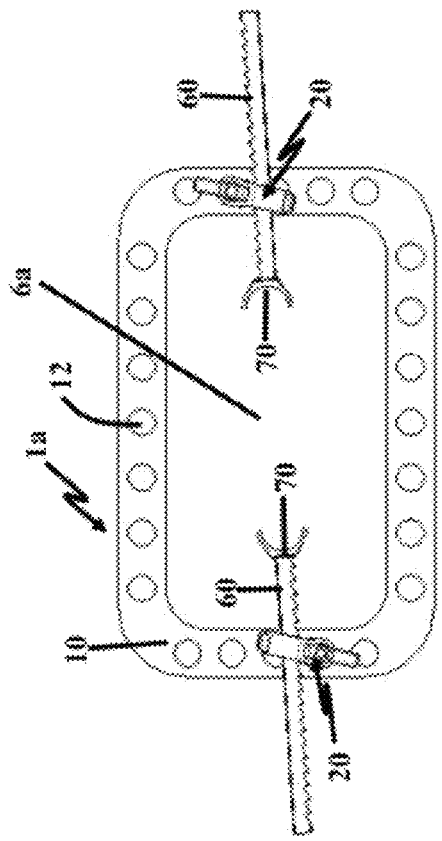
Figure 2C:
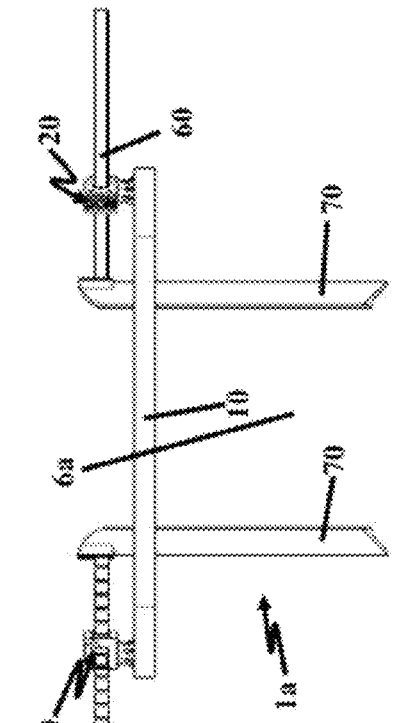
Figure 2D:
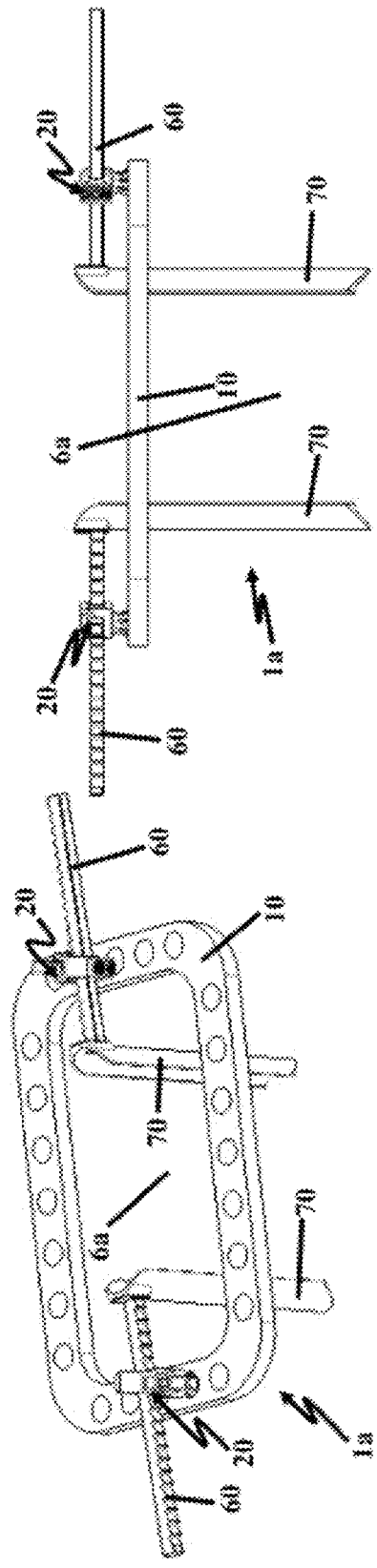
Figure 14A:
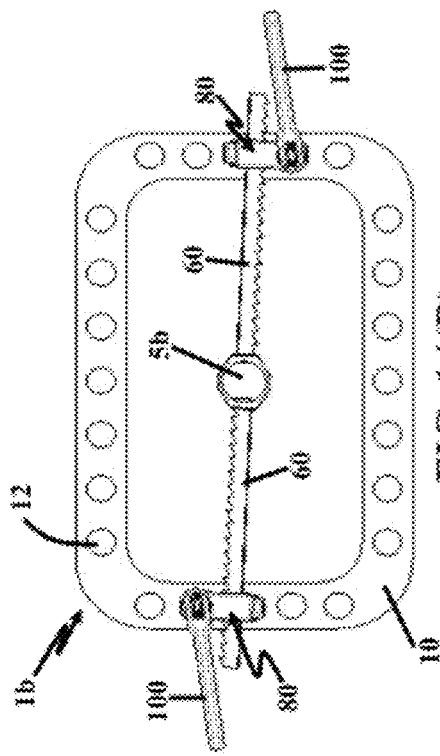
FIGS. 14(A) through 14(D) illustrate an adjustable polyaxial tissue retraction device, with two blades and a threaded securing mechanism, in a closed configuration, according to an embodiment described herein.
Figure 14B:
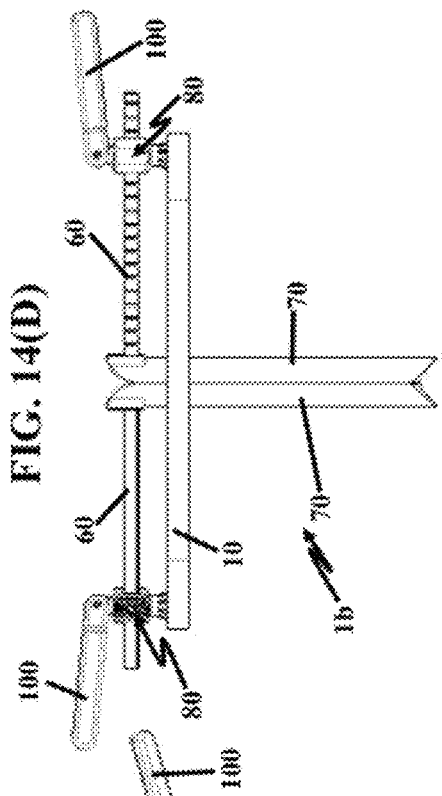
Figure 14C:
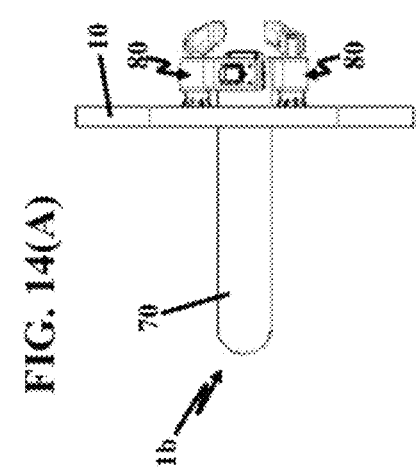
Figure 14D:
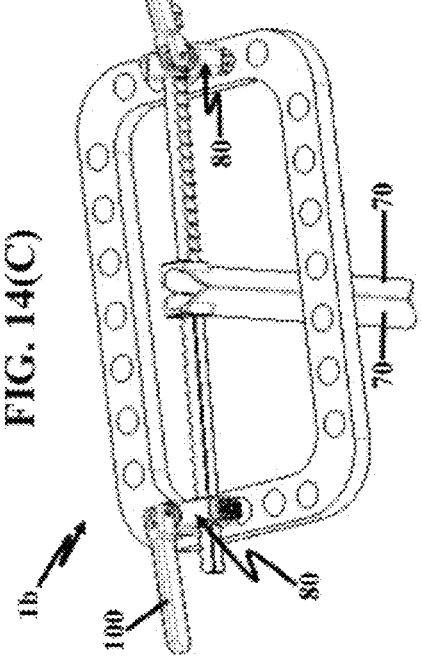

As discussed above, there remains a need to retract tissue during a surgical procedure with a surgical device that offers a greater degree of freedom (e.g., four degrees of freedom) than what is currently available. The embodiments herein achieve this by providing an adjustable polyaxial tissue retraction device, which includes a push-down connection assembly connected to a base plate that allows a surgeon to position the push-down connection assembly in any of three dimensions to thereby providing three degrees of freedom to a surgeon. An additional degree of freedom is supplied by a retraction bar connected to the push-down connection assembly to provide independent linear translation movement to the surgeon. Referring now to the drawings, and more particularly to FIGS. 1(A) through 22, where similar reference characters denote corresponding features consistently throughout the figures, there are shown preferred embodiments.

FIGS. 1(A) through 2(D), with reference to FIGS. 5(A) through 6(D), illustrate different perspective views of an adjustable polyaxial tissue retraction device 1a, in a closed and opened configuration. As shown, adjustable polyaxial tissue retraction device 1a includes base plate 10, push-down connection assembly 20, retraction bar 60, and retraction blade 70. Although not illustrated in FIGS. 1(A) through 2(D), but described in further detail below, each push-down connection assembly 20 includes a connector 20a, a push-down handle 30, a quick release mechanism 40, and a saddle pin 50. In addition, shown in FIGS. 1(A) through 2(D) are several sockets 12 cut into base plate 10. As discussed in further detail below, each socket 12 can accommodate one push-down connection assembly 20 therein.

Push-down connection assembly 20 provides a surgeon three degrees of freedom by allows the surgeon to lock push-down connection assembly 20 in three dimensions (e.g., in a vertical, horizontal, and depth dimension) by coupling push-down connection assembly 20 to any available socket 12 on base plate 10. Locking push-down connection assembly 20 is discussed in further detail below. Retraction bar 60 is also coupled to push-down connection assembly 20, as well as retraction blade 70. As shown in FIGS. 1(C), 1(D), 2(C), and 2(D), retraction bar 60 contains a number of teeth 17 on one side. As described further below, the teeth 17 embedded on one side of retraction bar 60 could be a one-sided buttress type mechanism to thereby resist forces in one direction only. For example, push-down connection assembly 20 is configured in FIGS. 1(A) through 2(D) to allow retraction bar 60 and retraction blade 70 to easily retract from the closed configuration shown in FIGS. 1(A) through 1(D) into the open configuration shown in FIGS. 2(A) through 2(D).

In addition, adjustable polyaxial tissue retraction device 1a is shown in FIGS. 1(A) through 2(D) with two push-down connection assemblies 20. In the closed configuration shown in FIGS. 1(A) through 1(D), each fully extended retraction bar 60 is illustrated as forming part of a perimeter of dynamic opening 5a where each portion of the perimeter is formed by retraction blade 70. Consequently, when the retraction bars are fully extended, dynamic opening 5a, which is formed by the retraction blades 70, can be easily accommodated into a small incision. Moreover, when the retraction bars 60 are retracted from the closed configuration shown in FIGS. 1(A) through 1(D), dynamic opening 6a, formed by the retraction blades 70 shown in FIGS. 2(A) through 2(D), is increased to a larger configuration when compared to dynamic opening 5a. While embodiments shown in FIGS. 2(A) through 2(D) illustrate the translative movement of the retraction blades 70 to be symmetrical, adjustable polyaxial tissue retraction device 1a is not limited to symmetrical movement and each retraction bar 60 or retraction blade 70 may be translated differently to provide an asymmetrical working areas for the surgeon. For example, when one retraction bar 60 is retracted independent of other retraction bars 60, an asymmetrical opening is formed by each retraction blade 70. Thus, adjustable polyaxial tissue retraction device 1a provides a surgeon with both symmetrical and asymmetrical working areas.

Shown in FIGS. 3(A) through 4(D), with reference to FIGS. 1(A) through 2(D) and FIGS. 5(A) through 6(D), are schematic diagrams of a base plate 10. As shown, top surface 11 forms a perimeter around base plate 10 and is etched with a plurality of sockets 12. The number of sockets 12 etched into base plate 10 and dimensions of each socket 12 may vary according to different surgical requirements. Each configuration of base plate 10, however, will allow a surgeon to choose any location with an open socket 12 along the perimeter of base plate 10 to attach push-down connection assembly 20, as described in further detail below. Moreover, since retraction blade 70 is securely coupled to retraction bar 60 and retraction bar 60 is coupled to push-down connection assembly 20, a surgeon is given significant freedom when positioning retraction blade 70, and how to form a working area composed of each retraction blade 60 taken together, by choosing a location to secure push-down connection assembly 20.

The shape of base plate 10 shown in FIGS. 3(A) through 4(D) is roughly rectangular. Other shapes are possible (e.g., circular, elliptical, etc), however, and base plate 10 is not limited to the shape shown in FIGS. 3(A) through 4(D). In addition, FIG. 3(C) illustrates a cross-sectional view of base plate 10 along the B-B axis shown in FIG. 3(B) and shows base plate 10 with a flat cross-section along the B-B axis. Alternatively, FIG. 4(C) illustrates a cross-sectional view of base plate 10 along the B-B axis shown in FIG. 4(B) and shows base plate 10 with a concaved cross-section along the B-B axis. In both FIGS. 3(D) and 4(D), base plate 10 is shown with a flat cross-section along the A-A axis shown in FIGS. 3(B) and 4(B), respectively. Other configuration are possible (e.g., the A-A axis may have a concaved cross-section in either FIG. 3(B) or 4(B)), and base plate 10 is not limited to the configuration shown.

FIGS. 5(A) through 11(D), with reference to FIGS. 1(A) through 4(D) and FIGS. 10(A) through 10(C), illustrate a push-down connection assembly 20 in a both a closed and open configuration. As mentioned above, push-down connection assembly 20 includes connector 20*a*, push-down handle 30, quick release mechanism 40, saddle pin 50, and retraction bar 60. Together, connector 20*a*, push-down handle 30 and saddle pin 50 constitute a push-down locking mechanism for push-down connection assembly 20. According to an embodiment described in further detail below, push-down connection assembly 20 is easily moved and adjusted on base plate 10 by a surgeon before or during a surgical procedure.

Once a surgeon has chosen a desired socket 12 along the perimeter of base plate 10 to secure push-down connection assembly 20, the surgeon secures push-down connection assembly 20 by using the push-down locking mechanism described above. FIGS. 5(A) through 11(D) illustrate push-down connection assembly 20 and the operation of the push-down locking mechanism. The push-down locking mechanism, for push-down engagement with base plate 10, includes push-down handle 30 attached to saddle pin 50 and optionally includes a detachable push-down assistance rod 65 that provides additional assistance to the surgeon when securing push-down connection assembly 20. To lock push-down connection assembly 20 to base plate 10, a surgeon engages saddle pin 50 with connector 20*a* via a vertical translation of push-down handle 30. To unlock push-down connection assembly 20 from the base plate 10, a surgeon simply disengages saddle pin 50 from connector 20*a* via a vertical translation of push-down handle 30. The vertical translation of saddle pin 50, via push-down handle 30, allows saddle pin 50 to engage or disengage itself with bulbous body 25. Moreover, as shown in FIGS. 5(B) and 5(D), when saddle pin 50 is engaged with bulbous body 25, blunt end 55 of saddle pin 50 (illustrated in FIGS. 10(A) through 10(C)) optionally completes the spherical form of bulbous body 25. The nature of bulbous body 25, as described in further detail below, allows push-down connection assembly 20 to be positioned and secured with three degrees of freedom. Consequently, when saddle pin 50 is firmly engaged in the locked position, the connection between base plate 10 and push-down connection assembly 20 is secured.

FIGS. 7(A) through 7(D), with reference to FIGS. 8(A) through 11(D), illustrates various views of connector 20*a*. As shown, main body 21 includes various cavities and channels cut therein. In particular, main body 21 includes quick release cavity 22, retraction bar channel 23, saddle pin channel 24, a number of rivet channels 27, and push-down handle axis channel 28. Each channel or cavity is configured to securely mate with another component of the complete push-down connection assembly 20. Specifically, quick release cavity 22 is configured to mate with a quick release mechanism 40 (illustrated in FIGS. 9(A) through 9(D), and described below). Retraction bar channel 23 is configured to mate with a retraction bar 60 (illustrated in FIGS. 11(A) through 11(D), and described below). Saddle pin channel 24 is configured to mate with a push-down saddle pin 50 (illustrated in FIGS. 10(A) through 10(D), as described below). Rivets 27 are configured to mate with rivet channels 47 used to support quick release mechanism 40 (illustrated in FIGS. 9(A) through 9(C), as described below). Finally, push-down handle axis channel 28 is configured to mate with a push-down handle axis pin (not shown).

In addition to the various cavities and channels described above, FIGS. 7(A) through 7(D) also illustrates connector 20*a* including bulbous body 25. Bulbous body 25 is optionally molded from the same material as main body 21 along a substantially lower planer surface of main body 21. Bulbous body 25 is shown as an expandable bulbous (or generally spherical) male body for engaging any concave female socket 12 of base plate 10. In addition, a plurality of axially spaced slots 26*a* are shown, cut into bulbous body 25 forming a plurality of flanges 26, which expand once saddle pin 50 is forced through saddle pin channel 24 and causing flanges 26 to outwardly project and expand. As a consequence, bulbous body 25 expands into any female spherical socket 12 of base plate 10 at any allowable angle and thereby securing connector 20*a* to base plate 10 via bulbous body 25.

Connector 20*a* also includes sloped body 29, as illustrated in FIGS. 7(A) through 7(D), to support articulated movement from push-down handle 30 when coupled to connector 20*a* via push-down handle axis pin channel 28 push-down assistance. In particular, sloped body 29 has a downward slope suitable to accommodate push-down handle 30 when saddle pin 50 is disengaged from bulbous body 25 (as described further below) and to not interfere with the operation thereof. While sloped body 29 is shown with a 45-degree decline, slope body 29 is not limited to such a configuration and other angles are possible.

FIGS. 8(A) through 8(D), with reference to FIGS. 10(A) through 10(C), illustrates different views of push-down handle 30. As shown, push-down handle 30 includes main handle body 31, angled body 32, pivot channel 33, handle-to-saddle-pin channel 34 and locking saddle pin channel 35. Main handle body 31 is shown as a solid body with pivot channel 33, handle-to-saddle-pin channel 34 and locking saddle pin channel 35 bored therethrough. Since main handle body 31 is frequently subjected to upward and downward forces (associated with engaging and disengaging saddle pin 50, as described below), main handle body 31 is preferably manufactured from a material suitable to handle such forces. Examples include, but are not limited to, various metal alloys and composite materials, such as a thermoplastic composite material.

In addition to the strength provided by main body 31, angled body 32 allows a smooth transition of push-down handle 30 from an engaged state to a disengaged state. While shown with three angled surfaces, other configurations for angled body 32 are possible (e.g., two angled surfaces or a uniform semi-spherical surface). Moreover, a smooth transition from one state to another is further assisted by pivot channel 33 and push-down handle pin (not shown). When assembled, push-down handle pin is embedded in pivot channel 33 of push-down handle 30 and push-down handle axis channel 28 of connector 20*a* to allow a smooth vertical translation of push-down handle 30. Handle-to-saddle-pin channel 34 is configured to mate with upper portion 51 of saddle pin 50 (shown in FIGS. 10(A) through 10(C)) and become locked in place via a handle securing pin (not shown) inserted through locking saddle pin channel 35 and locking channel 52 in saddle pin 50 (shown in FIGS. 10(A) through 10(D)). In addition, saddle pin 50 is etched with grooves 53 to secure saddle pin 50 in handle-to-saddle-pin channel 34. When saddle pin 50 is secured to push-down handle 30 with a handle-securing pin, any vertical force applied to push-down handle 30 is transferred to saddle pin 50 which effectuates a vertical translation of saddle pin 50 consistent with the vertical translation of push-down handle 30.

FIGS. 10(A) through 10(D), with reference to FIGS. 1(A) through 9(D), illustrate saddle pin 50. As shown, saddle pin 50 includes an upper fastening portion 51 and a lower tip portion 54. Upper fastening portion 51 further includes locking channel 52 and grooves 53. As shown, grooves 53 together cut upper fastening portion 51 into a square shape, which is configured to mate with handle-to-saddle-pin channel 34. The handle securing pin described above securely fits into both locking channel 52 and locking saddle pin channel 35 to securely couple saddle pin 50 with saddle handle 30. Those skilled in the art would recognize that other configurations are possible—for example, grooves 53 may form upper fastening portion 51 into a hexagonal or any other polygonal shape or may form a linear slit or cross-slit across the top of upper fastening portion 51.

As shown in FIGS. 10(A) through 10(C), lower portion 54 of threaded saddle pin 50 forms tapered section 55 and optionally terminates as blunt end 56. Tapered section 55 is configured to mechanically assist the expansion of bulbous body 25 from a closed position (as illustrated in FIGS. 5(A) through 5(D)) to an open position (as illustrated in FIGS. 6(A) through 6(D)). As illustrated in FIG. 6(D), optional blunt end 56 is configured to completely occupy the expanded terminating end of saddle pin channel 24 in bulbous body 25 to complete the spherical form of the expanded bulbous body 25.

Saddle pin 50 may also comprise a multi-part assembly. For example, the upper fastening portion 51 of saddle pin 50 may comprise titanium and the lower tip portion 54 of saddle pin 50 may comprise a ceramic material. Additionally, the lower tip portion 54 may comprise a mechanically harder material than the upper fastening portion 51. In such a configuration, retraction bar 60 and base plate 10 may optionally comprise a first material, and the lower tip portion 54 of saddle pin 50 may comprise a material having a higher material hardness and compressive yield strength than the first material. Moreover, adjustable polyaxial tissue retraction device 1a may further comprise a wear resistant ceramic coating (not shown) over connector 20a and base plate 10 to ensure durability and consistent performance over the lifetime of the device.

To assist a surgeon in effectuating the vertical translation of saddle pin 50, adjustable polyaxial tissue retraction device 1a may optionally include push-down assistance rod 65, illustrated in FIGS. 13(A) through 13(D), with reference to FIGS. 1(A) through 12(D). As shown, push-down assistance rod 65 includes upper portion 66, lower portion 67 and a plurality of grooves 68 that form assistance socket 69. Assistance socket 69 is configured to mate with grooves 53 of saddle pin 50. While grooves 68 is shown as forming a square shaped assistance socket 69, other configurations are possible and the shape of assistance socket 69 is not limited to what is shown in FIGS. 13(A) through 13(D). In addition, upper portion 66 is illustrated as a uniform cylindrical form. While not shown, other configurations for upper portion 66 are possible; for example, FIG. 13(C) may show upper portion 66 having a "T" shaped cross-section instead of a rectangular cross-section. When upper portion 66 is configured with a "T" shaped cross-section, a surgeon is given a greater area (namely, the top of upper portion 66 would provide a greater area that that shown in FIG. 12(B)), and greater comfort, to apply a downward force to saddle pin 50.

An additional degree of freedom is provided by adjustable polyaxial tissue retraction device 1a (illustrated in FIGS. 1(A) through 2(D)) via quick release mechanism 40 and retraction bar 60. FIGS. 9(A) through 9(D), with reference to FIGS. 1(A) through 8(D), illustrate various view of quick release mechanism 40. As shown, quick release mechanism 40 includes main quick release body 41, textured cap 42, a plurality of grooves 43 etched into textured cap 42, bar cavity 44, a plurality of teeth 45 formed within bar cavity 44, spring cavity 46 and a plurality of rivet channels 47. Quick release mechanism 40 is configured to mate with quick release cavity 22 of connector 20a and to accommodate a horizontal translation of quick release mechanism 40 within quick release cavity 22. The horizontal translation of quick release mechanism 40 within quick release cavity 22 is guided by rivet channels 47 bored through main quick release body 41 and coupled to rivets 27 (illustrated in FIGS. 7(A) through 7(D)) driven through connector 20a. Although rivet channels 47 are elliptically shaped in FIGS. 9(A) and 9(B) to accommodate the horizontal translation of quick release mechanism 40, other configurations are possible to accommodate the same or similar movements and rivet channels 47 are not limited to the shapes shown. Moreover, the horizontal movement of quick release mechanism 40 is effectuated by spring 49, which sits in spring cavity 46. As shown in FIGS. 5(B) and 6(B), one end of spring 49 is pressed against spring cavity 46 while the other end of spring 49 is pressed against flat surface 63 of retraction bar 60 (as illustrated in FIGS. 11(A) through 11(D)). When a surgeon applies pressure textured cap 42, which is securely coupled to main quick release body 41, the horizontal force is transferred to spring 49 resulting in spring 49 compressing. Consequently, when a surgeon ceases applying pressure to textured cap 42, compressed spring 49 releases its elastic energy and forces quick release mechanism 40 back to it original configuration.

Quick release mechanism 40 also includes locking teeth 45 configured to mate with retraction bar teeth 17 (illustrated in FIGS. 11(A) through 11(C)) of retraction bar 60. When locking teeth 45 are engaged with retraction bar teeth 17, retraction bar 60 is locked in place and no further lateral movement of retraction bar 60 is possible. After spring 49 is compressed, locking teeth 45 become disengaged from retraction bar teeth 17. Consequently, when locking teeth 45 are disengaged from retraction bar teeth 17, retraction bar 60 is free to move laterally.

FIGS. 11(A) through 11(D) illustrate various views of retraction bar 60. As shown, retraction bar 60 includes main retraction bar body 61, retraction bar teeth 17 and flat surface 63. In addition, as shown in FIGS. 11(A) and 11(D), each tooth of retraction bar teeth 17 includes a leading slope 64 and a trailing edge 62. Leading slope 64 and trailing edge 62 form a ratchet-type tooth configuration for retraction bar teeth 17 and allows movement in only one direction; namely the direction of leading slope 64. When retraction bar teeth 17 are engaged with the locking teeth 45 of quick release mechanism 40, retraction bar 60 is prevented from retracting. In addition, retraction bar 60 is securely coupled to retraction blade 70 (illustrated in FIGS. 12(A) through 12(D)). As a result of the lateral movement possible when locking teeth 45 are disengaged from retraction bar teeth 17, a surgeon may laterally alter the position of retraction blade 70 (illustrated in FIGS. 12(A) through 12(D)) and thereby altering the shape of the dynamic opening 5a (illustrated in FIGS. 1(A) through 2(D)) to accommodate a surgeon's needs during surgery.

FIGS. 12(A) through 12(D), with reference to FIGS. 1(A) through 11(D), illustrate various views of retraction blade 70. FIG. 12(A) is a side perspective view of main body 71 of retraction blade 70 with edges 74, convexed end 72, and socket 73. Socket 73 is configured to securely mate with one end of retraction bar 60 so that retraction bar 60 and retraction blade 70 move in unison. As shown, socket 73 is a square cavity cut into retraction blade 70. Other configurations of socket 73 are possible, however, and socket 73 is not limited to the shape shown in FIGS. 12(A) through 12(D). Optionally, edges 71 are notched so each can accommodate an adjacent retraction blade 70. FIG. 12(B) is a plan view of retraction blade 70 to further illustrate the convexed end 72. FIG. 12(C) is a side elevation view of retraction blade 70 that also shows the convexed end 72. FIG. 12(D) is a top view of retraction blade 70 that shows edges 71.

FIGS. 14(A) through 15(D), with reference to FIGS. 1(A) through 13(D) and 16(A) through 20(D), illustrate different perspective views of another embodiment of the adjustable polyaxial tissue retraction device 1b, with two retraction blades 70 and two threaded connection assemblies 80. FIGS. 14(A) through 14(D) show adjustable polyaxial tissue retraction device 1b in a closed configuration, while FIGS. 15(A) through 15(D) show adjustable polyaxial tissue retraction device 1b in an opened configuration. As shown, adjustable polyaxial tissue retraction device 1b includes base plate 10, threaded connection assembly 80, retraction bar 60, and retraction blade 70. In addition, while not illustrated in FIGS. 14(A) through 15(D), threaded connection assembly 80 includes threaded connector 80a, quick release mechanism 40, threaded saddle pin 90 and threaded saddle handle 100. Together, threaded connector 80a, threaded saddle pin 90 and threaded saddle handle 100 constitute a threaded locking mechanism. As with adjustable polyaxial tissue retraction device 1a shown in FIGS. 1(A) through 2(D), base plate 10 is shown with a plurality of sockets 12. As discussed above with respect to FIGS. 3(A) through 4(D), each socket 12 in base plate 10 accommodates a threaded connection assembly 80.

Threaded connection assembly 80 provides a surgeon three degrees of freedom by allowing the surgeon to lock threaded connection assembly 80 in three dimensions (e.g., in a vertical, horizontal and depth dimension) by coupling threaded connection assembly 80 to any available socket 12 on base plate 10. Locking threaded connection assembly 80 is discussed in further detail below. In addition, retraction bar 60 is coupled to threaded connection assembly 80, as well as retraction blade 70. As shown in FIGS. 14(C), 14(D), 15(C), and 15(D), and discussed in FIGS. 11(A) through 11(D) retraction bar 60 contains a number of ratchet-type teeth 17 on one side. The teeth 17 of retraction bar 60 are optionally configured as a one-sided buttress type mechanism and thereby resist forces in one direction only. For example, threaded connection assembly 80 is configured in FIGS. 14(A) through 15(D) to allow retraction bar 60 and retraction blade 70 to easily retract from the closed configuration shown in FIGS. 14(A) through 14(D) into the open configuration shown in FIGS. 15(A) through 15(D).

In addition, adjustable polyaxial tissue retraction device 1b is shown in FIGS. 14(A) through 15(D) with two threaded connection assemblies 80. In the closed configuration shown in FIGS. 14(A) through 14(D), each fully extended retraction bar 60 is illustrated as forming part of a perimeter of dynamic opening 5b where each portion of the perimeter is formed by retraction blade 70. Consequently, when retraction bars 60 are fully extended, dynamic opening 5b, formed by retraction blades 70, is easily accommodated in a small incision. Moreover, when retraction bars 60 are retracted from the closed configuration shown in FIGS. 14(A) through 14(D), dynamic opening 6b, formed by retraction blades 70 shown in FIGS. 15(A) through 15(D), is a larger opening compared to dynamic opening 5b. While embodiments shown FIGS. 15(A) through 15(D) illustrate the translative movement of retraction blades 70 to be symmetrical, adjustable polyaxial tissue retraction device 1b is not limited to symmetrical movement and each retraction bar 60 or retraction blade 70 may be translated differently to provide asymmetrical working areas for the surgeon. For example, when one retraction bar 60 is retracted independently of other retraction bars 60, an asymmetrical opening is formed by each retraction blade 70. Thus, adjustable polyaxial tissue retraction device 1b provides a surgeon with both symmetrical and asymmetrical working areas.

FIGS. 16(A) through 20(D), with reference to FIGS. 1(A) through 15(D) illustrate a threaded connection assembly 80, in a both a closed and open configuration. As mentioned above, threaded connection assembly 80 includes connector 80a, quick release mechanism 40, threaded saddle pin 90, retraction bar 60, and optionally threaded saddle handle 100. According to an embodiment described in further detail below, threaded connection assembly 80 is easily moved and adjusted on base plate 10 by a surgeon before or during a surgical procedure.

Once a surgeon has chosen a desired socket 12 along the perimeter of base plate 10 to secure threaded connection assembly 80, the surgeon secures threaded connection assembly 80 by using threaded saddle handle 100 to secure threaded saddle pin 90. FIGS. 16(A) through 20(D) illustrate various views of the different components that constitute threaded connection assembly 80. The mechanisms for threaded engagement includes threaded saddle handle 100 attached to threaded saddle pin 90. To lock threaded connection assembly 80 to base plate 10, a surgeon engages threaded saddle pin 90 with threaded connector 80a via a first torque applied to threaded saddle pin 90 via threaded saddle handle 100. To unlock threaded connection assembly 80 from the base plate 10, a surgeon simply disengages threaded saddle pin 90 from threaded connector 80a via a second torque (in a direction counter to the first torque) applied to threaded saddle pin 90 via threaded saddle handle 100. Through the torque applied to threaded saddle pin 90 via threaded saddle handle 100, a vertical translation of threaded saddle pin 90 is realized that allows threaded saddle pin 90 to engage or disengage itself with bulbous body 86 (shown in FIGS. 18(A) through 18(D)). As show, in FIGS. 16(B) and 16(D), when saddle pin 90 is engaged with bulbous body 86, blunt end 97 (illustrated in FIGS. 20(A) through 20(C)) completes the spherical form of bulbous body 86. The nature of bulbous body 86, as described in further detail below, allows threaded connection assembly 80 to be positioned and secured with three degrees of freedom. Consequently, when threaded saddle pin 90 is firmly engaged in the locked position, the connection between base plate 10 and threaded connection assembly 80 is secured.

FIGS. 18(A) through 18(D), with reference to FIGS. 1(A) through 17(D), illustrate various views of threaded connector 80a. As shown, main body 81 includes various cavities and channels cut therein. In particular, main body 81 includes quick release cavity 82, retraction bar channel 83, saddle pin channel 84, threads 85 etched into an inner surface of saddle pin channel 84, and a plurality of rivets 87. Each channel or cavity is configured to securing mate with another component of the complete threaded connection assembly 80. Specifically, quick release cavity 82 is configured to mate with a quick release mechanism 40 (illustrated in FIGS. 9(A) through 9(D), and described above). Retraction bar channel 83 is configured to mate with a retraction bar 60 (illustrated in FIGS. 11(A) through 11(D), and described above). Saddle pin channel 84 is configured to mate with a threaded saddle pin 90

(illustrated in FIGS. 19(A) through 19(D), as described below). Finally, rivets 87 are configured to mate with rivets channels 47 used to support quick release mechanism 40 (illustrated in FIGS. 9(A) through 9(D) and described above).

In addition to the various cavities and channels described above, FIGS. 18(A) through 18(D) also illustrates threaded connector 80a including bulbous body 86. Bulbous body 86 is optionally molded from the same material as main body 81 along a substantially lower planer surface of main body 81. Bulbous body 86 is shown as an expandable bulbous (or generally spherical) male body for engaging any concave female socket 12 of base plate 10. In addition, a plurality of axially spaced slots 89 are shown, cut into bulbous body 86 forming a plurality of flanges 88, which expand once threaded saddle pin 90 is forced through saddle pin channel 84 and causing flanges 88 to outwardly project and expand. As a consequence, bulbous body 86 expands into any female spherical socket 12 of base plate 10 at any allowable angle and thereby securing threaded connector 80a to base plate 10 via bulbous body 86.

Threaded connector 80a also includes threads 85 etched into saddle pin channel 84. Threads 85 are configured to mate with corresponding saddle threads 94 etched onto the outer perimeter of threaded saddle pin 90 (illustrated in FIGS. 19(A) through 19(D), and discussed below). When mated, the threads 85 and saddle threads 94 translate the torque applied to saddle pin 90 (optionally via saddle handle 100) into a vertical translation of saddle pin 90 and thereby engaging or disengaging saddle pin 90 from bulbous body 86.

FIGS. 20(A) through 20(B), with reference to FIGS. 1 through 19(D), illustrate threaded saddle pin 90. As shown, threaded saddle pin 90 includes an upper fastening portion 91 and a lower tip portion 95. Upper fastening portion 91 further includes locking channel 92, grooves 93 and saddle threads 94. As shown, grooves 93 together cut upper fastening portion 91 into a square shape, which is configured to mate with socket 104. Handle-to-saddle pin (not shown) securely fits in both locking channel 92 and handle-to-saddle-pin channel 105 to securely couple threaded saddle pin 90 with threaded saddle handle 100. Those skilled in the art would recognize that other configurations are possible—for example, grooves 93 may form upper fastening portion 91 into a hexagonal or any other polygonal shape or may form a linear slit or cross-slit across the top of upper fastening portion 91.

Lower portion 95 of threaded saddle pin 90 forms a tapered section 96 and optionally terminates as blunt end 97. Tapered section 96 is configured to mechanically assist the expansion of bulbous body 86 from a closed position (as illustrated in FIGS. 14(A) through 14(D)) to an open position (as illustrated in FIGS. 15(A) through 15(D)). As illustrated in FIG. 15(D), optional blunt end 97 is configured to completely occupy the expanded terminating end of saddle pin channel 84 in bulbous body 86 to complete the spherical form of the expanded bulbous body 86.

Threaded saddle pin 90 may also comprise a multi-part assembly. For example, the upper fastening portion 91 of saddle pin 90 may comprise titanium and the lower tip portion 95 of the saddle pin 90 may comprise a ceramic material. Additionally, the lower tip portion 95 may comprise a mechanically harder material than the upper fastening portion 91. In such a configuration, retraction bar 60 and base plate 10 may optionally comprise a first material, and the lower tip portion 95 of saddle pin 90 may comprise a material having a higher material hardness and compressive yield strength than the first material. Moreover, adjustable polyaxial tissue retraction device 1b may further comprise a wear resistant ceramic coating (not shown) over threaded connector 80a and base plate 10 to ensure durability and consistent performance over the lifetime of the device.

To assist a surgeon in effectuating the vertical translation of threaded saddle pin 90, adjustable polyaxial tissue retraction device 1b may optionally include threaded saddle handle 100, illustrated in FIGS. 19(A) through 19(D). As shown, threaded saddle handle 100 includes upper portion 101, lower portion 102, a plurality of handle arms 103 that form socket 104 and handle-to-saddle-pin channel 105. Socket 104 is configured to mate with grooves 93 of threaded saddle pin 90 and handle-to-saddle pin (not shown) secures threaded saddle handle 100 to threaded saddle pin 90. While handle arms 103 are shown as forming approximately a square shaped socket 104, other configurations are possible and the shape of socket 104 is not limited to what is shown in FIGS. 19(A) through 19(D).

FIGS. 21(A) through 21(D), with reference to FIGS. 1(A) through 20(D), illustrate different perspective views of an adjustable polyaxial tissue retraction device 1c in an opened configuration. As shown, adjustable polyaxial tissue retraction device 1c includes base plate 10, push-down connection assembly 20, retraction bar 60, and retraction blade 70. In FIGS. 21(A) through 21(D), six push-down connection assemblies 20, six retraction bars 60 and six retraction blades 70 are shown. Similar to adjustable polyaxial tissue retraction device 1a, shown in FIGS. 1(A) through 2(D), each push-down connection assembly 20 includes connector 20a, push-down bar 30, quick release mechanism 40, and saddle pin 50. In addition, a number of sockets 12 are shown etched into base plate 10. As described above, each socket 12 accommodates a single push-down connection assembly 20.

While adjustable polyaxial tissue retraction device 1a is shown in FIGS. 1(A) through 2(D) with two push-down connection assemblies, adjustable polyaxial tissue retraction device 1c is shown in FIGS. 21(A) through 21(D) with six push-down connection assemblies. Although the connection and adjustment mechanism described for adjustable polyaxial tissue retraction device 1a equally applies to the push-down connection mechanism for adjustable polyaxial tissue retraction device 1c, the six push-down connection assemblies shown in FIGS. 21(A) through 21(D) offer greater freedom in forming dynamic opening 6c compared to two push-down connection assemblies. In addition, a surgeon may begin with a configuration similar to FIGS. 1(A) through 1(D); i.e., two retraction bars 60 are fully extended to form part of a perimeter of dynamic opening 5a where each portion of the perimeter is formed by retraction blade 70. When the two retraction bars 60 are fully extended to form dynamic opening 6a, as shown in FIGS. 2(A) through 2(D), dynamic opening 6a may be further shaped by including addition push-down connection assemblies to form asymmetrical dynamic opening 6c. Thus, in FIGS. 21(A) through 21(D), a total of six push-down connection assemblies have been utilized to form an asymmetrical working area.

FIG. 22, with reference to FIGS. 1 through 21, is a flow diagram illustrating a method of retracting tissue according to an embodiment herein, wherein the method comprises providing (110) a base plate (e.g., base plate 10) comprising a first socket (e.g., socket 12) and a second socket (e.g., socket 12). The next step involves providing (115) a first joint connection assembly (e.g., joint connection assembly 20 or 80) and a second joint connection assembly (e.g., joint connection assembly 20 or 80).

Each joint connection assembly (e.g., joint connection assembly 20 or 80) comprises a number of different components. A retraction bar (e.g., retraction bar 60) includes a plurality of etched teeth (e.g., etched teeth 17). A retraction blade (e.g., retraction blade 70) is coupled to the retraction bar (e.g., retraction bar 60). A connector (e.g., connector 20a or 80a) includes a quick release component cavity (e.g., quick release cavity 22 or 82) and an outwardly protruding and expandable bulbous body (e.g., bulbous body 25 or 86), where the bulbous body (e.g., bulbous body 25 or 86) is directly coupled to any of the first socket (e.g., socket 12) and the second socket (e.g., socket 12). A quick release component (e.g., quick release component 40) is operatively connected to the quick release component cavity (e.g., quick release cavity 22 or 82) and engaged with at least one tooth (e.g., etched teeth 17) of the retraction bar (e.g., retraction bar 60) via a retraction bar cavity (e.g., bar cavity 44), where the quick release component (e.g., quick release component 40) is configured to loosely mate with the quick release component cavity (e.g., quick release cavity 22 or 82). A saddle pin (e.g., saddle pin 50 or 90) is engaged within the connector (e.g., connector 20a or 80a) via a first channel (e.g., channel 24 or 84) bored through the connector (e.g., connector 20a or 81) and contacting the bulbous body (e.g., bulbous body 25 or 86) causing the bulbous body (e.g., bulbous body 25 or 86) to outwardly expand.

Next, the method comprises attaching (120) the first and second joint connection assemblies 20, 80 to the base plate 10, and securing (125) the first joint connection assembly (e.g., joint connection assembly 20 or 80) to the first socket (e.g., socket 12) and the second joint connection assembly (e.g., joint connection assembly 20 or 80) to the second socket (e.g. socket 12) by inserting the saddle pin (e.g., saddle pin 50 or 90) through a channel (e.g., channel 24 or 84) bored through the first joint connection assembly (e.g., joint connection assembly 20 or 80) causing the bulbous body (e.g., bulbous body 25 or 86) of the first joint connection assembly (e.g., joint connection assembly 20 or 80) to outwardly expand into the first socket (e.g. socket 12) and causing the bulbous body (e.g., bulbous body 25 or 86) of the second joint connection assembly (e.g., joint connection assembly 20 or 80) to outwardly expand into the second socket (e.g. socket 12). Next, the method involves adjusting (130) the retraction blades (e.g., retraction blade 70) through adjustment of the retraction bars (e.g., retraction bar 60) via the quick release mechanisms (e.g., quick release component 40), where engagement of the quick release mechanisms (e.g., quick release component 40) prevents the retraction bars (e.g., retraction bar 60) from adjustment in a first longitudinal direction and allows adjustment of the retraction bars (e.g., retraction bar 60) in a second longitudinal direction opposite of the first longitudinal direction, and where disengagement of the quick release mechanism (e.g., quick release component 40) allows adjustment of the retraction bars (e.g., retraction bar 60) in the first and the second longitudinal directions.

The embodiments herein provide optimal placements for a tissue retraction device 1a, 1b, 1c. Most conventional assemblies do not allow the change of the orientation in four degrees of freedom for an individual tissue retraction device. The embodiments described herein provide, for example, surgical access to the thoracic and lumbar spine from a posterior and posterior lateral approach with minimal soft tissue disruption. Since the embodiment described herein provide a joint connection assembly, which offers three degrees of freedom, and a retraction bar 60, which offers one degree of freedom, the adjustable polyaxial tissue retraction device 1a, 1b, 1c described herein allow a surgeon to have not only variety choice of location but also the accommodating individual patient anatomy.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A system for retracting tissue, said system comprising:
   a retraction bar including a plurality of teeth etched therein;
   a retraction blade coupled to said retraction bar;
   a connector including a quick release component cavity and an outwardly protruding and expandable round bulbous body;
   a quick release component engaged with at least one tooth of said retraction bar via a retraction bar cavity, where said quick release component is configured to loosely mate with said quick release component cavity;
   a saddle pin engaged within said connector via a first channel bored through said connector and contacting said bulbous body causing said bulbous body to outwardly expand; and
   a base including a plurality of sockets embedded therein and directly connected to said bulbous body, wherein said base receives said connector.

2. The system of claim 1, wherein a longitudinal cross-section of said base is concaved.

3. The system of claim 1, wherein said base comprises a socket that cups said expandable bulbous body of said connector.

4. The system of claim 1, wherein said saddle pin comprises a push-down saddle pin including a grooved upper portion and a smooth lower portion, and wherein said lower portion included a tapered section.

5. The system of claim 4, further comprising:
   a push-down handle;
   a pivoting channel bored through said push-down handle;
   an axis channel bored through said connector;
   a pivoting pin configured to mate with said pivoting channel and said axis channel and thereby allowing said push-down handle to pivot with respect to said connector;
   a saddle-handle channel bored through said push-down handle, wherein said grooved upper portion of said push-down saddle pin is configured to mate with said saddle-handle channel;
   a locking saddle pin channel bored through said grooved upper portion of said push-down saddle pin; and
   a locking saddle pin configured to mate with said saddle-handle channel and said locking saddle pin channel.

6. The system of claim 4, further comprising a push-down assistance rod including an assistance socket, where said assistance socket is configured to mate with said grooved upper portion of said push-down saddle pin.

7. The system of claim 1, wherein said saddle pin comprises a threaded saddle pin including a lower portion and a threaded upper portion that is configured to mate with threads embedded in said first channel.

8. The system of claim 7, further comprising:
   a locking channel bored through said threaded upper portion;
   a threaded saddle handle;

a saddle-handle pin channel bored through said threaded saddle handle; and
a saddle-handle pin configured to mate with said locking channel and said saddle handle pin channel.

9. The system of claim 1, wherein said quick release component includes an upper portion and a lower portion, wherein said retraction bar cavity is cut into said lower portion.

10. The system of claim 9, further comprising:
a spring cavity cut into said lower portion of said quick release component; and
a spring embedded into said spring cavity.

11. The system of claim 10, further comprising:
a plurality of rivets, fixedly coupled to said quick-release component cavity of said connector; and
a plurality of rivet channels, equal to the number of said rivets and bored through said lower portion of said quick release component,
wherein each of said rivet channels is configured to mate with one of said rivets and said rivet channels allow lateral movement of said rivets.

12. The system of claim 9, further comprising concentric grooves etched onto an outer surface of said upper portion of said quick release component.

13. A system for retracting tissue, said system comprising:
a retraction bar including a plurality of teeth etched therein;
a retraction blade including a retraction bar socket bored through said retraction blade and configured to securely mate with said retraction bar;
a connector including a quick release component cavity and an outwardly protruding and expandable round bulbous body;
a quick release component engaged with at least one tooth of said retraction bar via a retraction bar cavity, where said quick release component is configured to loosely mate with said quick release component cavity;
a saddle pin engaged within said connector via a first channel bored through said connector and contacting said bulbous body causing said bulbous body to outwardly expand, said saddle pin including an upper portion and a lower portion;
a handle coupled to said saddle pin; and
a base including a plurality of sockets embedded therein and directly connected to said bulbous body, wherein said base receives said connector.

14. The system of claim 13, wherein said bulbous body comprises a plurality of slots separating a plurality of bendable flanges of said bulbous body.

15. The system of claim 13, further comprising a plurality of connectors, wherein each connector includes an outwardly protruding and expandable round bulbous body coupled to a socket on said base.

16. The system of claim 13, wherein said connector comprises a substantially planar lower surface, wherein said bulbous body extends from said lower surface of said connector, and wherein a socket of said plurality of sockets embedded in said base cups said expandable bulbous body.

17. The system of claim 13, further comprising:
a pivoting channel bored through said handle;
a push-down handle axis channel bored through said connector;
a pivoting pin configured to mate with said pivoting channel and said axis channel and thereby allowing said handle to pivot with respect to said connector;
a saddle-handle channel bored through said handle, wherein said upper portion of said saddle pin is configured to mate with said saddle-handle channel;
a locking saddle pin channel bored through said upper portion of said saddle pin; and
a locking saddle pin configured to mate with said saddle-handle channel and said locking saddle pin channel.

18. The system of claim 13, wherein said first channel is etched with first channel threads, and wherein said upper portion of said saddle pin is embedded with saddle pin threads configured to mate with said first channel threads.

19. The system of claim 18, further comprising:
a locking channel bored through said upper portion of said saddle pin;
a saddle-handle pin channel bored through said handle; and
a saddle-handle pin configured to mate with said locking channel and said saddle handle pin channel.

* * * * *